United States Patent [19]

Obata et al.

[11] Patent Number: 5,498,612
[45] Date of Patent: Mar. 12, 1996

[54] 4-PHENETHYLAMINOPYRIMIDINE DERIVATIVE, AND AGRICULTURAL AND HORTICULTURAL CHEMICAL FOR CONTROLLING NOXIOUS ORGANISMS CONTAINING THE SAME

[75] Inventors: Tokio Obata; Katsutoshi Fujii; Akira Ooka; Yoshinori Yamanaka, all of Ube, Japan

[73] Assignee: Ube Industries, Ltd., Yamaguchi, Japan

[21] Appl. No.: 380,717

[22] Filed: Jan. 30, 1995

[30] Foreign Application Priority Data

Feb. 1, 1994 [JP] Japan ..................... 6-010688

[51] Int. Cl.[6] ................ C07D 239/30; C07D 239/42; A01N 43/54
[52] U.S. Cl. ................ 514/256; 514/63; 544/229; 544/327; 544/328; 544/329; 544/326
[58] Field of Search ................ 544/229, 327, 544/328, 329, 326; 514/63, 256

[56] References Cited

U.S. PATENT DOCUMENTS

| | | | |
|---|---|---|---|
| 4,435,402 | 3/1984 | Tsuji et al. | 544/326 |
| 4,895,849 | 1/1990 | Yoshioka et al. | 514/252 |
| 4,994,616 | 2/1991 | Munro | 564/346 |
| 5,141,941 | 8/1992 | Fujii et al. | 514/256 |
| 5,280,025 | 1/1994 | Obata et al. | 544/326 |
| 5,378,708 | 1/1995 | Drumm et al. | 514/256 |

FOREIGN PATENT DOCUMENTS 59-36666  2/1984  Japan.
4-225976  8/1992  Japan.

*Primary Examiner*—John M. Ford
*Attorney, Agent, or Firm*—Finnegan, Henderson, Farabow, Garrett & Dunner

[57] ABSTRACT

Disclosed are a 4-phenethylaminopyrimidine compound represented by the formula (I):

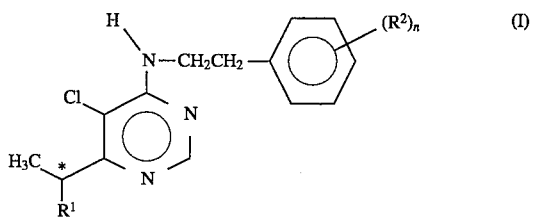

wherein $R^1$ represents halogen, hydroxyl, acyloxy, alkoxy, haloalkoxy, alkylthio, benzyloxycarbonyloxy, alkyloxycarbonyloxy, alkylsulfonyloxy, tri(alkyl)silyloxy or alkyloxycarbonylalkyloxy;

$R^2$ represents hydrogen, alkyl, alkoxy, halogen, haloalkyl, haloalkoxy, unsubstituted or substituted benzoyl, hydroxyl, haloalkylcarbonyl, alkylsulfonyloxy, haloalkylsulfonyloxy, alkylsulfonyl, alkylsulfinyl, haloalkylsulfinyl, tri(alkyl)silylalkoxy, alkylthio, unsubstituted or substituted pyridyloxy, unsubstituted or substituted phenoxy, alkenyloxy, haloalkenyloxy, unsubstituted or substituted benzyl, 2-phenyl-2-1,3-dioxolanyl, alkoxyiminobenzyl, nitro, haloalkylthio or alkynyloxy; n is an integer of 1 to 5 and * represents an asymmetric carbon atom.

a process for preparing the same and an agricultural and horticultural chemical for controlling noxious organisms which contains the same as an active ingredient.

8 Claims, No Drawings

4-PHENETHYLAMINOPYRIMIDINE DERIVATIVE, AND AGRICULTURAL AND HORTICULTURAL CHEMICAL FOR CONTROLLING NOXIOUS ORGANISMS CONTAINING THE SAME

BACKGROUND OF THE INVENTION

This invention relates to a novel 4-phenethylaminopyrimidine derivative which is an agricultural and horticultural chemical for controlling noxious organisms useful as an insecticide, an acaricide, a fungicide and a nematocide.

As a 4-phenethylaminopyrimidine derivative similar to the 4-phenethylaminopyrimidine derivative of the present invention, the following compounds have been known.

(1) In Japanese Provisional Patent Publication No. 176967/1982 (which corresponds to U.S. Pat. No. 4,435,402), it has been described that a compound represented by the following formula:

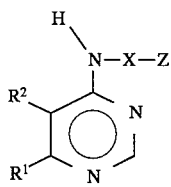

wherein $R^1$ and $R^2$ each represent a lower alkyl group or a halogen atom; X represents an alkylene group; and Z represents a substituted or unsubstituted phenyl group (a substituent(s) is/are one or two substituent(s) selected from a halogen, a lower alkyl and a lower alkoxy), a furyl group or a thienyl group; provided that the definitions of $R^1$ $R^2$ X and Z are limited only to the above formula, is effective for an insecticide, an acaricide and a fungicide.

(2) In Japanese Provisional Patent Publication No. 36666/1984, it has been described that a compound represented by the following formula:

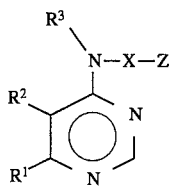

wherein $R^1$ and $R^2$ each represent a lower alkyl group or a halogen atom, or $R^1$ and $R^2$ are combined to represent a trimethylene group or a tetramethylene group; $R^3$ represents a hydrogen atom or a lower alkyl group; X represents an alkylene group; and Z represents a substituted or unsubstituted phenyl group (a substituent (s) is/are one or two substituent (s) selected from a halogen, a lower alkyl and a lower alkoxy), a furyl group or a thienyl group; provided that the definitions of $R^1$ to $R^3$, X and Z are limited only to the above formula, is effective for an insecticide, an acaricide and a fungicide.

(3) In Japanese Provisional Patent Publication No. 225364/1988 (which corresponds to U.S. Pat. No. 4,895,849), it has been described that a compound represented by the following formula:

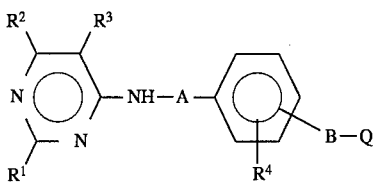

wherein $R^1$ represents a hydrogen atom or a lower alkyl group which is unsubstituted or substituted by a halogen atom; $R^2$ and $R^3$ each independently represent a halogen atom or a lower alkyl group which is unsubstituted or substituted by a halogen atom, a lower alkoxy group or a lower alkylthio group; $R^4$ represents a hydrogen atom, a halogen atom or a lower alkyl group; Q represents a phenyl group or a heterocyclic group, each of which is unsubstituted or substituted by a halogen atom, a nitro group, a lower alkoxy group, a lower alkylthio group, a lower alkyl group which is unsubstituted or substituted by a halogen atom or a lower alkoxy group, a phenyl group which is unsubstituted or substituted by a lower alkoxy group, or a phenoxy group which is unsubstituted or substituted by a halogen atom or a lower alkyl group which is unsubstituted or substituted by a halogen atom; the heterocyclic group may be substituted by an oxo group; A represents a lower alkylene group which is substituted by one or two substituent(s) selected from the group consisting of a cycloalkyl group having 3 to 5 carbon atoms, a lower alkynyl group and a lower alkyl group which is unsubstituted or substituted by a halogen atom, a lower alkoxy group or a lower alkylthio group; and B represents a direct bond, an oxygen atom, a sulfur atom, a straight or branched lower alkylene group or a lower alkyleneoxy group; provided that the definitions of $R^1$ to $R^4$A, B and Q are limited only to the above formula, is effective for an insecticide, an acaricide and a fungicide.

(4) In Japanese Provisional Patent Publication No. 68362/1989 (which corresponds to U.S. Pat. No. 4,994,616), it has been described that a compound represented by the following formula:

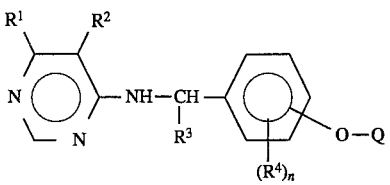

wherein $R^1$ and $R^2$ each independently represent a halogen atom or a lower alkyl group; $R^3$ represents a lower alkyl group or a cycloalkyl group having 3 to 5 carbon atoms; $R^4$ represents a halogen atom or a lower alkyl group; n represents 0, 1 or 2; and Q represents an alkyl group having 5 to 10 carbon atoms, an allyl group, a geranyl group, a farnesyl group, a lower alkyl group substituted by 1 to 4 halogen atoms, a cycloalkylmethyl group having 3 to 6 carbon atoms, a lower alkoxy group, an ethyl group substituted by a phenoxy group which is substituted by a lower alkoxyalkyl group, a lower alkylthio group, a lower alkylsulfonyl group or 1 or 2 lower alkyl group(s), a glycidyl group, an acetonyl group, a dioxolanylmethyl group substituted by a phenoxymethyl group which may be unsubstituted or substituted by a chlorine atom, a 2,2-diethoxyethyl group, a 1-ethoxycarbonylethyl group, a trimethylsilylmethyl group, a 1-pyridylethyl group, or a lower alkyl group substituted by a benzylimino group which may be substituted by a lower alkoxyimino group or a lower alkyl group; provided that the definitions of $R^1$ to $R^4$, Q and n are limited only to the above formula, is effective for an insecticide, an acaricide and a fungicide.

(5) In Japanese Provisional Patent Publication No. 7267/1991 (which corresponds to U.S. Pat. No. 5,141,941), it has been described that a compound represented by the following formula:

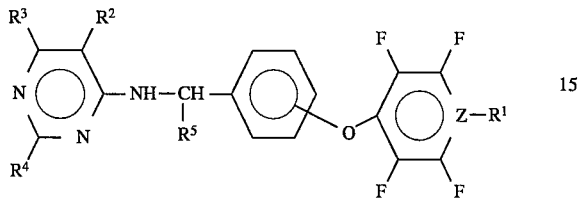

wherein $R^1$ represents a hydrogen atom, a halogen atom, a halo-lower alkyl group, an alkanoyl group, a nitro group, a cyano group or a 1,3-dioxolan-2-yl group; $R^2$ and $R^3$ each represent a halogen atom or a lower alkyl group, or $R^2$ and $R^3$ are condensed to a pyrimidine ring with carbon atoms to which they are bonded to represent an unsaturated 5- or 6-membered ring which may have one sulfur atom constituting the ring; $R^4$ represents a hydrogen atom, a halogen atom, a lower alkyl group, a cycloalkyl group or an amino group which may be substituted by a lower alkoxy group or a lower alkyl group; $R^5$ represents a hydrogen atom, a lower alkyl group or a cycloalkyl group; and Z represents a carbon atom or a nitrogen atom; provided that the definitions of $R^1$ to $R^5$ and Z are limited only to the above formula, is effective for a fungicide.

(6) In Japanese Provisional Patent Publication No. 163066/1991 (which corresponds to U.S. Pat. No. 5,141,941), it has been described that a compound represented by the following formula:

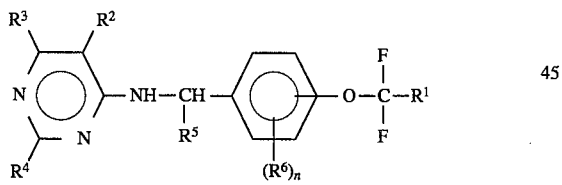

wherein $R^1$ represents a hydrogen atom or a halogen atom; $R^2$ and $R^3$ each represent a hydrogen atom, a halogen atom or a lower alkyl group, or $R^2$ and $R^3$ are condensed to a pyrimidine ring with carbon atoms to which they are bonded to represent a saturated or unsaturated 5- or 6-membered ring which may have one sulfur atom constituting the ring; $R^4$ represents a hydrogen atom, a halogen atom, a lower alkyl group, a cycloalkyl group, a lower alkoxy group, a lower alkylthio group or an amino group which may be substituted by a lower alkyl group; $R^5$ represents a hydrogen atom, a lower alkyl group, a cycloalkyl group or a halo-lower alkyl group; $R^6$ represents a hydrogen atom, a halogen atom, a lower alkyl group, a lower alkoxy group or a halo-lower alkoxy group; and n represents an integer of 1 or 2; provided that the definitions of $R^1$ to $R^6$ and n are limited only to the above formula, is effective for an insecticide and an acaricide.

(7) In Japanese Provisional Patent Publication No. 225976/1992, it has been described that a compound represented by the following formula:

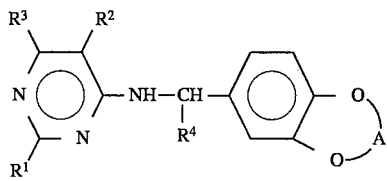

wherein $R^1$ represents a hydrogen atom, a lower alkyl group or a halogen atom; $R^2$ represents a halogen atom; and $R^3$ represents a lower alkyl group; or $R^2$ and $R^3$ are condensed to a pyrimidine ring with carbon atoms to which they are bonded to represent a saturated or unsaturated 5- or 6-membered ring which may have one sulfur atom; $R^4$ represents a hydrogen atom, a lower alkyl group or a cycloalkyl group; and A represents a methylene group or an ethylene group each of which is substituted by 1 to 4 halogen atoms; provided that the definitions of $R^1$ to $R^4$ and A are limited only to the above formula, is effective for a fungicide.

(8) In Japanese Provisional Patent Publication No. 201999/1993 (which corresponds to U.S. Pat. No. 5,280,025), it has been described that a compound represented by the following formula:

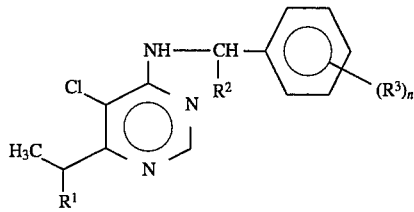

wherein $R^1$ represents a halogen atom, a lower acyloxy group, a hydroxyl group, a lower alkoxy group or a lower alkylthio group; $R^2$ represents a lower alkyl group, a hydrogen atom or a cycloalkyl group; $R^3$ represents a lower haloalkoxy group, a hydrogen atom, a lower alkyl group, a lower alkoxy group, a halogen atom, a lower alkylthio group, a nitro group, a lower haloalkyl group, a lower alkylsulfinyl group, a lower alkylsulfonyl group, a lower haloalkylthio group or a hydroxyl group; and n represents an integer of 1 to 5; provided that the definitions of $R^1$ to $R^3$ and n are limited only to the above formula, is effective for an insecticide, an acaricide, a fungicide and a nematocide.

However, there has not been disclosed a 4-β-phenethylamino-pyrimidine derivative in which an ethyl group at 6-position of a pyrimidine ring is substituted as in the present invention.

Thus, the 4-phenethylaminopyrimidine derivative of the present invention is a novel compound and it has not been known that the 4-phenethylaminopyrimidine derivative of the present invention has an activity of controlling noxious organisms for agriculture and horticulture such as an insecticidal, acaricidal, fungicidal or nematocidal activity.

SUMMARY OF THE INVENTION

An object of the present invention is to provide a novel 4-phenethylaminopyrimidine derivative, a process for preparing the same and an agricultural and horticultural chemical for controlling noxious organisms containing said derivative as an active ingredient, which is useful as an insecticide, an acaricide, a fungicide and a nematocide.

The present inventors have studied intensively in order to achieve the above object and consequently found that a novel 4-phenethylaminopyrimidine derivative has remarkable controlling activities such as insecticidal, acaricidal, fungicidal and nematocidal activities, which is useful as an agricultural and horticultural chemical for controlling noxious organisms, to accomplish the present invention.

That is, a first invention relates to a 4-phenethylaminopyrimidine derivative represented by the following formula (I):

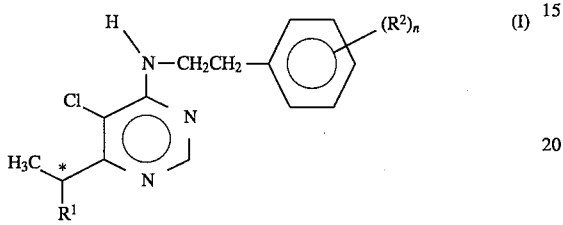

wherein $R^1$ represents a halogen atom, a hydroxyl group, an acyloxy group having 2 to 5 carbon atoms, an alkoxy group having 1 to 4 carbon atoms, a haloalkoxy group having 1 to 4 carbon atoms, an alkylthio group having 1 to 4 carbon atoms, a benzyloxycarbonyloxy group, an alkyloxycarbonyloxy group having 2 to 5 carbon atoms, an alkylsulfonyloxy group having 1 to 4 carbon atoms, a tri(C1-4 alkyl)silyloxy group or an alkyloxycarbonyl-alkyloxy group having 3 to 6 carbon atoms;

$R^2$ represents a hydrogen atom, an alkyl group having 1 to 4 carbon atoms, an alkoxy group having 1 to 4 carbon atoms, a halogen atom, a haloalkyl group having 1 to 4 carbon atoms, a haloalkoxy group having 1 to 4 carbon atoms, 'a benzoyl group which is unsubstituted or substituted by at least one of a halogen atom, an alkyl group having 1 to 4 carbon atoms, an alkoxy group having 1 to 4 carbon atoms, a haloalkyl group having 1 to 4 carbon atoms and an alkylthio group having 1 to 4 carbon atoms, a hydroxyl group, a haloalkylcarbonyl group having 2 to 5 carbon atoms, an alkylsulfonyloxy group having 1 to 4 carbon atoms, a haloalkylsulfonyloxy group having 1 to 4 carbon atoms, an alkylsulfonyl group having 1 to 4 carbon atoms, an alkylsulfinyl group having 1 to 4 carbon atoms, a haloalkylsulfinyl group having 1 to 4 carbon atoms, a tri(C1-4 alkyl)silylalkoxy group having 1 to 4 alkoxy carbon atoms, an alkylthio group having 1 to 4 carbon atoms, a pyridyloxy group which is unsubstituted or substituted by at least one of a halogen atom and a haloalkyl group having 1 to 4 carbon atoms, a phenoxy group which is unsubstituted or substituted by at least one of a halogen atom and a haloalkyl group having 1 to 4 carbon atoms, an alkenyloxy group having 2 to 5 carbon atoms, a haloalkenyloxy group having 2 to 5 carbon atoms, a benzyl group which is unsubstituted or substituted by at least one of a halogen atom and a hydroxyl group, a 2-phenyl-2-1,3-dioxolanyl group, an alkoxyiminobenzyl group, a dialkylhydrazonobenzyl group, a nitro group, a haloalkylthio group having 1 to 4 carbon atoms, or an alkynyloxy group having 2 to 5 carbon atoms;

n is an integer of 1 to 5; and
* represents an asymmetric carbon atom.

A second invention relates to a process for preparing the 4-phenethylaminopyrimidine derivative represented by the above formula (I), which comprises reacting a pyrimidine derivative represented by the following formula (II):

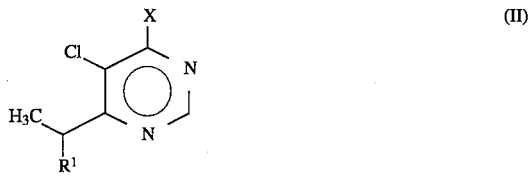

wherein $R^1$ has the same meaning as defined above; and X represents a halogen atom, with a 4-β-phenethylamine represented by the following formula (III):

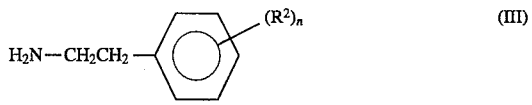

wherein $R^2$ and n have the same meanings as defined above.

A third invention relates to an agricultural and horticultural chemical for controlling noxious organisms comprising the 4-phenethylaminopyrimidine derivative represented by the above formula (1) as an active ingredient and an insecticidally, acaricidally, fungicidally or nematocidally effective carrier.

DESCRIPTION OF THE PREFERRED EMBODIMENTS

In the following, the present invention is explained in detail.

Desired compounds and starting materials

In the novel 4-phenethylaminopyrimidine derivative (compound (I)) which is the desired compound and starting compounds thereof (compound (II) and compound (III)), $R^1$, $R^2$ and n are as described below.

($R^1$)

As $R^1$, there may be mentioned a halogen atom, a hydroxyl group, an acyloxy group having 2 to 5 carbon atoms, an alkoxy group having 1 to 4 carbon atoms, a haloalkoxy group having 1 to 4 carbon atoms, an alkylthio group having 1 to 4 carbon atoms, a benzyloxycarbonyloxy group, an alkyloxycarbonyloxy group having 2 to 5 carbon atoms, an alkylsulfonyloxy group having 1 to 4 carbon atoms, a tri($C_{1-4}$ alkyl)silyloxy group and an alkyloxycarbonylalkyloxy group having 3 to 6 carbon atoms As the halogen atom, there may be mentioned a chlorine atom, an iodine atom, a bromine atom and a fluorine atom, preferably a fluorine atom and a chlorine atom.

As the acyloxy group, there may be mentioned an acyloxy group with 2 to 5 carbon atoms having a straight or branched alkyl group, preferably those having 2 to 4 carbon atoms, more preferably an acetyloxy group (—OCOCH$_3$).

As the alkoxy group, there may be mentioned a straight or branched alkoxy group having 1 to 4 carbon atoms, preferably a methoxy group (—OCH$_3$).

As the haloalkoxy group, there may be mentioned a straight or branched alkoxy group substituted by a halogen atom such as a chlorine atom, an iodine atom, a bromine atom and a fluorine atom, preferably —OCF$_2$CHFCF$_3$ and —OCF$_2$CHFCl.

As the alkylthio group, there may be mentioned an alkylthio group with 1 to 4 carbon atoms having a straight or branched alkyl group, preferably a methylthio group (—$SCH_3$).

As the alkyloxycarbonyloxy group, there may be mentioned an alkyloxycarbonyloxy group with a straight or branched alkyl group, preferably a tert-butoxycarbonyloxy group (—OCOO—t—$C_4H_9$).

As the alkylsulfonyloxy group, there may be mentioned an alkylsulfonyloxy group with a straight or branched alkyl group, preferably a methylsulfonyloxy group (—$OSO_2CH_3$).

As the tri(alkyl)silyloxy group, there may be mentioned a tri (alkyl)silyloxy group with a straight or branched alkyl group, preferably a trimethylsilyloxy group (—OSi ($CH_3$)$_3$).

As the alkyloxycarbonylalkyloxy group, there may be mentioned an alkyloxycarbonylalkyloxy group with a straight or branched alkyl group, preferably a methoxycarbonyloxymethoxy group (—$OCH_2COOCH_3$).

($R^2$)

As $R^2$, there may be mentioned a hydrogen atom, an alkyl group having 1 to 4 carbon atoms, an alkoxy group having 1 to 4 carbon atoms, a halogen atom, a haloalkyl group having 1 to 4 carbon atoms, a haloalkoxy group having 1 to 4 carbon atoms, a benzoyl group, a hydroxyl group, a haloalkylcarbonyl group having 2 to 5 carbon atoms, an alkylsulfonyloxy group having 1 to 4 carbon atoms, a haloalkylsulfonyloxy group having 1 to 4 carbon atoms, an alkylsulfonyl group having 1 to 4 carbon atoms, an alkylsulfinyl group having 1 to 4 carbon atoms, a haloalkylsulfinyl group having 1 to 4 carbon atoms, a tri($C_{1-4}$ alkyl)silylalkoxy group having 1 to 4 alkoxy carbon atoms, an alkylthio group having 1 to 4 carbon atoms, a pyridyloxy group, a phenoxy group, an alkenyloxy group having 2 to 5 carbon atoms, a haloalkenyloxy group having 2 to 5 carbon atoms, a benzyl group, a 2-phenyl-2-1,3-dioxolanyl group, an alkoxyiminobenzyl group having 1 to 4 alkoxy carbon atoms, a di($C_{1-4}$ alkyl)hydrazonobenzyl group, a nitro group, a haloalkylthio group having 1 to 4 carbon atoms, or an alkynyloxy group having 2 to 5 carbon atoms.

As the number of n, there may be mentioned an integer of 1 to 5, and it is preferably 1 or 2. The substitution position of $R^2$ is not particularly limited, and it is preferably 3-position and/or 4-position. Other substitutable positions than $R^2$ on the phenyl ring are substituted by hydrogen atoms.

As the alkyl group, there may be mentioned a straight or branched alkyl group having 1 to 4 carbon atoms, preferably a methyl group.

As the alkoxy group, there may be mentioned a straight or branched alkoxy group having 1 to 4 carbon atoms, preferably a methoxy group (—$OCH_3$) and an ethoxy group (—$OC_2H_5$).

As the halogen atom, there may be mentioned a chlorine atom, an iodine atom, a bromine atom and a fluorine atom, preferably a fluorine atom and a chlorine atom.

As the haloalkyl group, there may be mentioned a straight or branched alkyl group substituted by a halogen atom such as a chlorine atom, an iodine atom, a bromine atom and a fluorine atom, preferably a trifluoromethyl group (—$CF_3$).

As the haloalkoxy group, there may be mentioned a straight or branched alkoxy group substituted by a halogen atom such as a chlorine atom, an iodine atom, a bromine atom and a fluorine atom, preferably —$OCF_3$, —$OCHF_2$, —$OCH_2CF_3$, —$OCF_2CHFCF_3$, —$OCHFCHF_2$ and —$OCF_2CHFCl$.

As the benzoyl group, there may be mentioned an unsubstituted or substituted benzoyl group.

The substitution position of the benzoyl group is not particularly limited, but it is preferably 4-position.

As the halogen atom to be used as a substituent for the benzoyl group, there may be mentioned a chlorine atom, an iodine atom, a bromine atom and a fluorine atom, preferably a fluorine atom and a chlorine atom.

As the alkyl group to be used as a substituent for the benzoyl group, there may be mentioned a straight or branched alkyl group having 1 to 4 carbon atoms, preferably a methyl group.

As the alkoxy group to be used as a substituent for the benzoyl group, there may be mentioned a straight or branched alkoxy group having 1 to 4 carbon atoms, preferably a methoxy group.

As the haloalkyl group to be used as a substituent for the benzoyl group, there may be mentioned a haloalkyl group with 1 to 4 carbon atoms having a straight or branched alkyl and a halogen atom such as a chlorine atom, an iodine atom, a bromine atom and a fluorine atom, preferably a trifluoromethyl group.

As the haloalkylcarbonyl group, there may be mentioned a haloalkylcarbonyl group wherein a haloalkyl group of which is a straight or branched one substituted by a halogen atom such as a chlorine atom, an iodine atom, a bromine atom and a fluorine atom, preferably a trifluoromethylcarbonyl group (—$COCF_3$).

As the alkylsulfonyloxy group, there may be mentioned an alkylsulfonyloxy group wherein an alkyl group of which is a straight or branched one, preferably a methylsulfonyloxy group (—$OS_2CH_3$).

As the haloalkylsulfonyloxy group, there may be mentioned a haloalkylsulfonyloxy group wherein an alkyl group of which is a straight or branched one substituted by a halogen atom such as a chlorine atom, an iodine atom, a bromine atom and a fluorine atom, preferably a trifluoromethylsulfonyloxy group (—$OSO_2CF_3$).

As the alkylsulfonyl group, there may be mentioned an alkylsulfonyl group wherein an alkyl group of which is a straight or branched one, preferably a methylsulfonyl group (—$SO_2CH_3$).

As the alkylsulfinyl group, there may be mentioned an alkylsulfinyl group wherein an alkyl group of which is a straight or branched one, preferably a methylsulfinyl group (—$SOCH_3$).

As the haloalkylsulfinyloxy group, there may be mentioned a haloalkylsulfinyloxy group wherein an alkyl group of which is a straight or branched one substituted by a halogen atom such as a chlorine atom, an iodine atom, a bromine atom and a fluorine atom, preferably a fluoromethylsulfinyloxy group (—$OSOCH_2F$).

As the tri(alkyl)silylalkoxy group, there may be mentioned a tri(alkyl)silylalkoxy group wherein an alkyl group of which is a straight or branched one, preferably a trimethylsilylmethoxy group (—$OCH_2Si(CH_3)_3$).

As the alkylthio group, there may be mentioned an alkylthio group wherein an alkyl group of which is a straight or branched one, preferably a methylthio group (—$SCH_3$).

As the pyridyloxy group, there may be mentioned an unsubstituted one or substituted by a halogen atom or a haloalkyl group having 1 to 4 carbon atoms.

The substitution position of the pyridyloxy group is not particularly limited, but it is preferably 2-position and/or 4-position.

As the halogen atom to be used as a substituent for the pyridyloxy group, there may be mentioned a chlorine atom, an iodine atom, a bromine atom and a fluorine atom, preferably a chlorine atom.

As the haloalkyl group to be used as a substituent for the pyridyloxy group, there may be mentioned a haloalkyl group wherein an alkyl group of which is straight or branched one substituted by a halogen atom such as a chlorine atom, an iodine atom, a bromine atom and a fluorine atom, preferably a trifluoromethyl group.

As the phenoxy group, there may be mentioned an unsubstituted one or substituted by a halogen atom or a haloalkyl group having 1 to 4 carbon atoms.

The substitution position of the phenoxy group is not particularly limited.

As the halogen atom to be used as a substituent for the phenoxy group, there may be mentioned a chlorine atom, an iodine atom, a bromine atom and a fluorine atom, preferably a chlorine atom or a fluorine atom.

As the haloalkyl group to be used as a substituent for the phenoxy group, there may be mentioned a haloalkyl group wherein an alkyl group of which is straight or branched one substituted by a halogen atom such as a chlorine atom, an iodine atom, a bromine atom and a fluorine atom, preferably a trifluoromethyl group.

As the alkenyloxy group, there may be mentioned a straight or branched alkenyloxy group, preferably an allyoxy group ($-OCH_2CH=CH_2$).

As the haloalkenyloxy group, there may be mentioned a haloalkenyloxy group wherein an alkenyl group of which is a straight or branched one substituted by a halogen atom such as a chlorine atom, an iodine atom, a bromine atom and a fluorine atom, preferably $-OCH=CH-CH=CF_2$ and $-OCH_2CH_2-CF=CF_2$.

As the benzyl group, there may be mentioned an unsubstituted benzyl group or a benzyl group substituted by a halogen atom or a hydroxyl group.

The substitution position of the benzyl group is not particularly limited, but preferably an α-position.

As the halogen atom to be used as a substituent for the benzyl group, there may be mentioned a chlorine atom, an iodine atom, a bromine atom and a fluorine atom, preferably a chlorine atom or a fluorine atom.

As the alkyloxyiminobenzyl group, there may be mentioned an alkoxyiminobenzyl group wherein an alkoxy group of which is a straight or branched alkoxy group, preferably a methoxy group ($-OCH_3$).

As the dialkylhydrazonobenzyl group, there may be mentioned a dialkylhydrazonobenzyl group wherein an alkyl group of which is a straight or branched alkyl group, preferably a methyl group ($-CH_3$).

As the haloalkylthio group, there may be mentioned a haloalkylthio group wherein an alkyl group of which is a straight or branched one substituted by a halogen atom such as a chlorine atom, an iodine atom, a bromine atom and a fluorine atom, preferably a 2,2,2-trifluoroethylthio group ($-SCH_2CF_3$).

As the alkynyloxy group, there may be mentioned a straight or branched one, preferably $-OCH_2C\equiv CH$.

As the compound (I), there may be mentioned compounds comprising a combination of various substituents described above. From the point of pharmaceutical effects, the following compounds are preferred:

(1) a compound in which $R^1$ is a halogen atom and $R^2$ is a hydrogen atom;
(2) a compound in which $R^1$ is a hydroxyl group and $R^2$ is a hydrogen atom;
(3) a compound in which $R^1$ is an acyloxy group having 2 to 5 carbon atoms and $R^2$ is an alkyl group having 1 to 4 carbon atoms;
(4) a compound in which $R^1$ is a hydroxyl group and $R^2$ is an alkyl group having 1 to 4 carbon atoms;
(5) a compound in which $R^1$ is a halogen atom and $R^2$ is an alkyl group having 1 to 4 carbon atoms;
(6) a compound in which $R^1$ is a halogen atom and $R^2$ is an alkoxy group having 1 to 4 carbon atoms;
(7) a compound in which $R^1$ is an acyloxy group having 2 to 5 carbon atoms and $R^2$ is an alkoxy group having 1 to 4 carbon atoms;
(8) a compound in which $R^1$ is a hydroxyl group and $R^2$ is an alkoxy group having 1 to 4 carbon atoms;
(9) a compound in which $R^1$ and $R^2$ are halogen atoms;
(10) a compound in which $R^1$ is a halogen atom and $R^2$ is a benzoyl group;
(11) a compound in which $R^1$ is an acyloxy group having 2 to 5 carbon atoms and $R^2$ is a benzoyl group;
(12) a compound in which $R^1$ is a hydroxyl group and $R^2$ is a benzoyl group;
(13) a compound in which $R^1$ is a halogen atom and $R^2$ is a haloalkyl group having 1 to 4 carbon atoms;
(14) a compound in which $R^1$ is a halogen atom and $R^2$ is a haloalkoxy group having 1 to 4 carbon atoms;
(15) a compound in which $R^1$ is an alkylthio group having 1 to 4 carbon atoms and $R^2$ is a benzoyl group;
(16) a compound in which $R^1$ is a halogen atom and $R^2$ is a haloalkylcarbonyl group having 2 to 5 carbon atoms;
(17) a compound in which $R^1$ is an acyloxy group having 2 to 5 carbon atoms and $R^2$ is an alkylsulfonyloxy group having 1 to 4 carbon atoms;
(18) a compound in which $R^1$ is a hydroxyl group and $R^2$ is an alkylsulfonyloxy group having 1 to 4 carbon atoms;
(19) a compound in which $R^1$ is a halogen atom and $R^2$ is an alkylsulfonyloxy group having 1 to 4 carbon atoms;
(20) a compound in which $R^1$ is an acyloxy group having 2 to 5 carbon atoms and $R^2$ is a haloalkoxy group having 1 to 4 carbon atoms;
(21) a compound in which $R^1$ is a hydroxyl group and $R^2$ is a haloalkoxy group having 1 to 4 carbon atoms;
(22) a compound in which $R^1$ is an alkoxy group having 1 to 4 carbon atoms and $R^2$ is a haloalkoxy group having 1 to 4 carbon atoms;
(23) a compound in which $R^1$ is a benzyloxycarbonyloxy group and $R^2$ is a haloalkoxy group having 1 to 4 carbon atoms;
(24) a compound in which $R^1$ is an alkyloxycarbonyloxy group having 2 to 5 carbon atoms and $R^2$ is a haloalkoxy group having 1 to 4 carbon atoms;
(25) a compound in which $R^1$ is a halogen atom and $R^2$ is a haloalkylsulfonyloxy group having 1 to 4 carbon atoms;
(26) a compound in which $R^1$ is an acyloxy group having 2 to 5 carbon atoms and $R^2$ is a haloalkylsulfonyloxy group having 1 to 4 carbon atoms;
(27) a compound in which $R^1$ is an alkylsulfonyloxy group having 1 to 4 carbon atoms and $R^2$ is a benzoyl group;
(28) a compound in which $R^1$ is a tri($C_{1-4}$ alkyl)silyloxy group and $R^2$ is a benzoyl group;
(29) a compound in which $R^1$ is an acyloxy group having 2 to 5 carbon atoms and $R^2$ is a haloalkyl group having 1 to 4 carbon atoms;
(30) a compound in which $R^1$ is a hydroxyl group and $R^2$ is a haloalkyl group having 1 to 4 carbon atoms;
(31) a compound in which $R^1$ is a halogen atom and $R^2$ is an alkoxyiminobenzyl group;
(32) a compound in which $R^1$ is a halogen atom and $R^2$ is a 2-phenyl-2-1,3-dioxolanyl group;
(33) a compound in which $R^1$ is a halogen atom and $R^2$ is a benzyl group;
(34) a compound in which $R^1$ is a haloalkoxy group having 1 to 4 carbon atoms and $R^2$ is a haloalkoxy group having 1 to 4 carbon atoms;

(35) a compound in which $R^1$ is a halogen atom and $R^2$ is a phenoxy group;
(36) a compound in which $R^1$ is a halogen atom and $R^2$ is a haloalkenyloxy group having 2 to 5 carbon atoms;
(37) a compound in which $R^1$ is a halogen atom and $R^2$ is an alkenyloxy group having 2 to 5 carbon atoms;
(38) a compound in which $R^1$ is a halogen atom and $R^2$ is a tri($C_{1-4}$ alkyl)silylalkoxy group having 1 to 4 alkoxy carbon atoms;
(39) a compound in which $R^1$ is a halogen atom and $R^2$ is an alkylthio group having 1 to 4 carbon atoms;
(40) a compound in which $R^1$ is a halogen atom and $R^2$ is a hydroxyl group;
(41) a compound in which $R^1$ is a halogen atom and $R^2$ is an alkylsulfonyl group having 1 to 4 carbon atoms;
(42) a compound in which $R^1$ is a halogen atom and $R^2$ is an alkylsulfinyl group having 1 to 4 carbon atoms;
(43) a compound in which $R^1$ is a halogen atom and $R^2$ is a pyridyloxy group;
(44) a compound in which $R^1$ is a halogen atom and $R^2$ is a haloalkylsulfinyl group having 1 to 4 carbon atoms;
(45) a compound in which $R^1$ is a halogen atom and $R^2$ is a dialkylhydrazonobenzyl group;
(46) a compound in which $R^1$ is a hydroxyl group and $R^2$ is an α-hydroxybenzyl group; and
(47) a compound in which $R^1$ is a halogen atom and $R^2$ is a nitro group.

As $R^1$ and $R^2$ in the compounds (I) shown in (1) to (45) comprising preferred combinations, there may be mentioned preferred examples and more preferred examples described above.

As these specific compounds (I), there may be mentioned Compounds 1 to 16, 18 to 29, 33, 34, 38 to 56, 58 to 93, 108 to 114 in Table 2 shown below.

The compound (I) of the present invention has an amino group so that an acid addition salt derived from the amino group is also included in the present invention.

As an acid forming the acid addition salt, there may be mentioned, for example, an inorganic acid such as hydrochloric acid, hydrobromic acid, nitric acid, sulfuric acid and phosphoric acid; a carboxylic acid such as formic acid, oxalic acid, fumaric acid, adipic acid, stearic acid, oleic acid and aconitic acid; an organic sulfonic acid such as methanesulfonic acid, benzenesulfonic acid and p-toluenesulfonic acid; and saccharin.

The compound (I) of the present invention has an asymmetric carbon atom represented by * in the formula (I) so that all of optical isomers and racemic compounds derived from the asymmetric carbon atom and a mixture of them are also included in the present invention.

Synthetic method of the compound (I)

As a preferred embodiment of preparing the 4-phenethylaminopyrimidine derivative represented by the above formula (I), there may be mentioned the following five preparation processes (Synthetic methods 2 to 6) in addition to Synthetic method 1 described as the second invention.

(Synthetic method 2)

A process for preparing the 4-phenethylaminopyrimidine derivative represented by the above formula (I) in which $R^1$ is a lower acyloxy group (referred to as compound (I-2)), which comprises reacting a 4-phenethylaminopyrimidine derivative represented by the following formula (I-1):

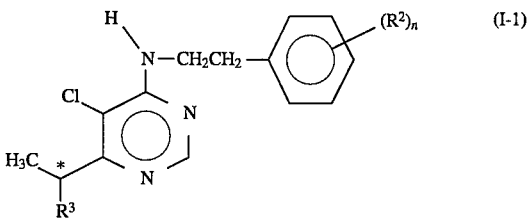

wherein $R^2$, n and * have the same meanings as defined above; and $R^3$ represents a halogen atom, with a lower aliphatic carboxylic acid represented by the following formula (IV):

$$R^4\text{—H} \qquad (IV)$$

wherein $R^4$ represents a lower acyloxy group.

(Synthetic method 3)

A process for preparing the 4-phenethylaminopyrimidine derivative represented by the above formula (I) in which $R^1$ is a hydroxyl group (referred to as compound (I-3)), which comprises reacting a 4-phenethylaminopyrimidine derivative represented by the following formula ( I-2):

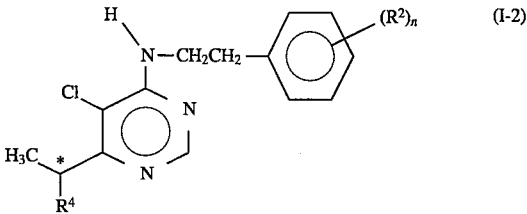

wherein $R^2$ $R^4$ n and * have the same meanings as defined above, with an inorganic base represented by the following formula (v):

$$M\text{—OH} \qquad (V)$$

wherein M represents an alkali metal.

(Synthetic method 4)

A process for preparing the 4-phenethylaminopyrimidine derivative represented by the above formula (I) in which $R^1$ is a lower alkoxy group (or a lower alkylthio group) (referred to as compound (I-4)), which comprises reacting the 4-phenethylaminopyrimidine derivative represented by the above formula (I-1) with an alcohol (or a mercaptan) represented by the following formula (VI):

$$R^5\text{—Y—H} \qquad (VI)$$

wherein $R^5$ represents a lower alkyl group; and Y represents an oxygen atom or a sulfur atom.

(Synthetic method 5)

A process for preparing the 4-phenethylaminopyrimidine derivative represented by the above formula (I) in which $R^1$ is a fluorine atom (referred to as compound (I-5)), which comprises reacting the 4-phenethylaminopyrimidine derivative represented by the above formula (I-1) with an alkali metal fluorine compound represented by the following formula (VII):

$$M\text{—F} \qquad (VII)$$

wherein M has the same meaning as defined above.

(Synthetic method 6)

A process for preparing the compound (I-5), which comprises reacting a 4-phenethylaminopyrimidine derivative represented by the following formula (I-3):

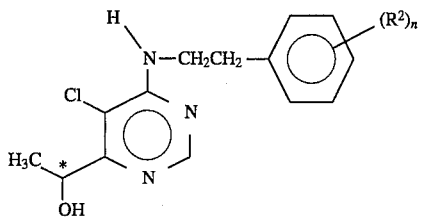

(I-3)

with a fluorinating agent represented by the following formula (VIII):

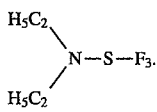

(VIII)

Synthetic methods 1 to 6 of the compound (I) of the present invention described above are described in detail.

(Synthetic method 1)

Synthetic method 1 is a method of obtaining the compound (I) by reacting the compound (II) with the compound (III) in the presence or absence of a solvent. The reaction can be accelerated by carrying out it in the presence of a base.

The solvent is not particularly limited so long as it does not participate in the present reaction directly and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; nitriles such as acetonitrile and propionitrile; organic bases such as triethylamine, pyridine and N,N-dimethylaniline; 1,3-dimethyl-2-imidazolidone; dimethyl sulfoxide; and a mixture of the above solvents.

The solvent may be used in such an amount that the concentration of the compound (II) becomes 5 to 80% by weight, preferably 10 to 70% by weight.

The base is not particularly limited and may include, for example, organic bases such as triethylamine, pyridine, N,N-dimethylaniline and 1,8-diazabicyclo[5.4.0]-7-undecene (DBU); alkali metal alkoxides such as sodium methoxide and sodium ethoxide; and inorganic bases such as sodium hydride, sodium amide, sodium hydroxide, potassium hydroxide, sodium carbonate, sodium hydrogen carbonate and potassium carbonate. Preferred are organic bases.

The amount of the base to be used may be 0.001 to 5 mole, preferably 0.8 to 2 mole per mole of the compound (II).

The reaction temperature is not particularly limited, but it may be in the temperature range of room temperature to a boiling point or lower of a solvent used, preferably 80° to 110° C.

The reaction time varies depending on the above concentration and temperature, but it is generally 0.3 to 4 hours.

The amount of the starting compound (III) to be used is 0.5 to 2 mole, preferably 1.0 to 1.2 mole per mole of the starting compound (II).

The compound (II) (when $R^1$ is X) to be used in the present invention can be prepared generally by reacting a compound (IX-1) with a compound (X-1) in a solvent as shown below in the same manner as in the method described in Japanese Provisional Patent Publication No. 194417/1993.

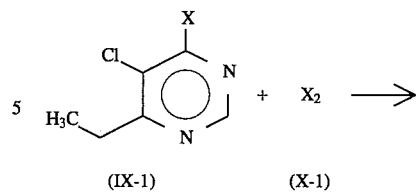

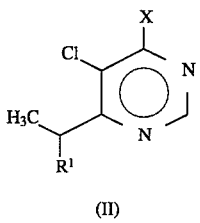

(II)

wherein $R^1$ is X; and X has the same meaning as defined above.

As the solvent, there may be mentioned the solvents as described above; and the solvent may be used in such an amount that the concentration of the compound (IX-I) becomes 5 to 80% by weight.

The reaction temperature is not particularly limited, but it may be in the temperature range of room temperature to a boiling point or lower of a solvent used.

The reaction time varies depending on the above concentration and temperature, but it is generally 2 to 10 hours.

The amount of the starting compound (X-i) to be used is 0.5 to 3 mole, preferably 0.5 to 1.7 mole per mole of the starting compound (IX-1).

The compound (IX-i) can be prepared as shown in the following scheme according to the method described in "Journal of Chemical Society" (J.C.S.), pp. 3478 to 3481 (1955).

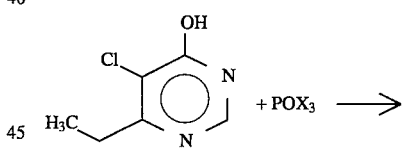

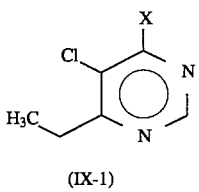

(IX-1)

wherein X has the same meaning as defined above.

After completion of the reaction, the compound (II) prepared as described above is subjected to common post-treatments such as extraction, condensation and filtration, and if necessary, it may be purified suitably by a known means such as recrystallization and various chromatographies.

As the compound (II), there may be mentioned Compounds (II-1) to (II-7) in Table 1 shown below.

The compound (III) to be used in the present invention can be prepared as shown in the following scheme:

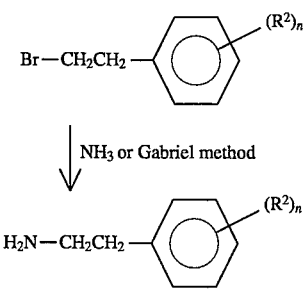

wherein $R^2$ and n have the same meanings as defined above.

As the compound (III), there may be mentioned compounds (III) comprising the respective kinds of substituents corresponding to Compounds 1 to 114 shown in Table 2 (referred to as Compounds $(III)_1$ to $(III)_{114}$ and, for example, Compound (III)1 is a compound represented by the formula (III) in which $R^2$ is a hydrogen atom and n is 1).

As the desired compound (I) synthesized as described above, there may be mentioned Compounds 1 to 114 shown in Table 2 (for example, Compound 1 is a compound represented by the formula (I) in which $R^1$ is a fluorine atom and $R^2$ is a hydrogen atom and n is 1).

(Synthetic method 2)

Synthetic method 2 is a method of obtaining the compound (I-2) (a compound represented by the formula (I) in which $R^1$ is a lower acyloxy group) by reacting the compound (I-1) with the compound (IV) in the presence or absence of a solvent. The reaction can be accelerated by carrying out it in the presence of a base.

As the solvent, there may be mentioned the solvents described in Synthetic method 1, aliphatic carboxylic acids such as acetic acid and propionic acid and a mixture of them, preferably N,N-dimethylformamide and an aliphatic carboxylic acid which is the same as an acryloxy group to be introduced.

The solvent may be used in such an amount that the concentration of the compound (I-1) becomes 5 to 80% by weight, preferably 10 to 70% by weight.

As the base, there may be mentioned the bases described in Synthetic method 1, preferably inorganic bases.

The amount of the base to be used may be 1 to 5 mole, preferably 2 to 5 mole per mole of the compound (I-1).

The reaction temperature is not particularly limited, but it may be in the temperature range of room temperature to a boiling point or lower of a solvent used, preferably 80 to 120° C.

The reaction time varies-depending on the above concentration and temperature, but it is generally 2 to 10 hours.

As the compound (IV), a commercially available product can be used.

After completion of the reaction, the desired compound (I-2) prepared as described above is subjected to common post-treatments such as extraction, condensation and filtration, and if necessary, it may be purified suitably by a known means such as recrystallization and various chromatographies.

As the compound (I-2), there may be mentioned Compounds 4, 8, 12, 19, 23, 27, 36, 45, 49, 56, 63, 66, 109 and 113 shown in Table 2.

(Synthetic method 3)

Synthetic method 3 is a method of obtaining the compound (I-3) (a compound represented by the formula (I) in which $R^1$ is a hydroxyl group) by reacting the compound (I-2) with the compound (V) in a solvent. The reaction can be accelerated by carrying out it in the presence of a base.

As the solvent, there may be mentioned the ethers, ketones and amides described in Synthetic method 1, alcohols such as methanol, ethanol, propanol and butanol, water and a mixture of the above solvents, preferably a mixture of an alcohol and water.

The solvent may be used in such an amount that the concentration of the compound (I-2) becomes 5 to 80% by weight, preferably 10 to 70% by weight.

As the base, there may be mentioned the inorganic bases described in Synthetic method 1, preferably sodium hydroxide and potassium hydroxide.

The amount of the base to be used may be 1 to 5 mole, preferably 2 to 5 mole per mole of the compound (I-2).

The reaction temperature is not particularly limited, but it may be in the temperature range of room temperature to a boiling point or lower of a solvent used, preferably room temperature to 50° C.

The reaction time varies depending on the above concentration and temperature, but it is generally 0.5 to 1 hour.

As the compound (V), a commercially available product can be used.

After completion of the reaction, the desired compound (I-3) prepared as described above is subjected to common post-treatments such as extraction, condensation and filtration, and if necessary, it may be purified suitably by a known means such as recrystallization and various chromatographies.

As the compound (I-3), there may be mentioned Compounds 2, 5, 9, 13, 20, 24, 28, 37, 46, 50, 57, 64, 67, 92, 110 and 114 shown in Table 2.

(Synthetic method 4)

Synthetic method 4 is a method of obtaining the compound (I-4) (a compound represented by the formula (I) in which $R^1$ is an alkoxy group having 1 to 4 carbon atoms or an alkylthio group having 1 to 4 carbon atoms) by reacting the compound (I-1) with the compound (VI) in the presence or absence of a solvent. The reaction can be accelerated by carrying out it in the presence of a base.

As the solvent, there may be mentioned the ethers, ketones and amides described in Synthetic method 1 and a mixture of the above solvents, preferably ketones and amides.

The solvent may be used in such an amount that the concentration of the compound (I-1) becomes 5 to 80% by weight, preferably 10 to 70% by weight.

As the base, there may be mentioned the bases described in Synthetic method 1, preferably inorganic bases.

The amount of the base to be used may be 1 to 5 mole, preferably 1 to 3 mole per mole of the compound (I-1).

The reaction temperature is not particularly limited, but it may be in the temperature range of room temperature to a boiling point or lower of a solvent used, preferably room temperature to 60° C.

The reaction time varies depending on the above concentration and temperature, but it is generally 0.3 to 2 hours.

As the compound (VI), a commercially available product can be used.

After completion of the reaction, the desired compound (I-4) prepared as described above is subjected to common post-treatments such as extraction, condensation and filtration, and if necessary, it may be purified suitably by a known means such as recrystallization and various chromatographies.

As the compound (I-4), there may be mentioned Compounds 39, 40, 52 and 89 shown in Table 2.

(Synthetic method 5)

Synthetic method 5 is a method of obtaining the compound (I-5) (a compound represented by the formula (I) in which $R^1$ is a fluorine atom) by reacting the compound (I-1) with the compound (VII) in a solvent. The reaction can be accelerated by carrying out it under heating.

As the solvent, there may be mentioned amides such as N,N-dimethylformamide and N,N-dimethylacetamide; 1,3-dimethyl-2-imidazolidone; dimethyl sulfoxide; sulforane; and a mixture of the above solvents.

The solvent may be used in such an amount that the concentration of the compound (I-1) becomes 5 to 80% by weight, preferably 10 to 70% by weight.

As the compound (VII), there may be mentioned an alkali metal fluorine compound, preferably cesium fluoride and potassium fluoride.

The ratio of the solvent to be used is 1 to 5 mole, preferably 1.2 to 3 mole per mole of the compound (I-1).

The reaction temperature is not particularly limited, but it may be in the temperature range of room temperature to a boiling point or lower of a solvent used, preferably 100° to 140° C.

The reaction time varies depending on the above concentration and temperature, but it is generally 1 to 8 hours.
(Synthetic method 6)

The compound (I-5) can be synthesized by a method other than Synthetic method 5, i.e., reacting the compound (I-3) with a fluorinating agent in a solvent.

Synthetic method 6 is a method of obtaining the compound (I-5) by reacting the compound (I-3) with a fluorinating agent.

As the solvent, there may be mentioned the chlorinated or unchlorinated aromatic, aliphatic or alicyclic hydrocarbons described in Synthetic method 1; ethers such as diethyl ether, tetrahydrofuran and dioxane and a mixture of the above solvents.

The solvent may be used in such an amount that the concentration of the compound (I-3) becomes 5 to 80% by weight, preferably 10 to 70% by weight.

The fluorinating agent is not particularly limited, and there may be used diethylaminosulfate trifluoride (DAST) represented by the following formula (VIII):

(VIII)

The amount of the fluorinating agent to be used may be 1 to 5 mole per mole of the compound (I-3), preferably 1 to 2 mole per mole of the compound (I-3).

The reaction temperature is not particularly limited, but it may be in the temperature range of ice cooling temperature to a boiling point or lower of a solvent used, preferably ice cooling temperature to room temperature.

The reaction time varies depending on the above concentration and temperature, but it is generally 0.3 to 2 hours.

After completion of the reaction, the desired compound (I-5) prepared by Synthetic method 5 or 6 is subjected to common post-treatments such as extraction, condensation and filtration, and if necessary, it may be purified suitably by a known means such as recrystallization and various chromatographies.

As the compound (I-5), there may be mentioned Compounds 1, 6, 10, 14, 15, 17, 21, 25, 29 to 34, 38, 43, 47, 51, 58, 68 to 71, 73 to 75, 77 to 88, 93 to 107 and 111 shown in Table 2.

AGRICULTURAL AND HORTICULTURAL CHEMICAL FOR CONTROLLING NOXIOUS ORGANISMS (Controlling effect)

As the agricultural and horticultural noxious organisms on which a controlling effect by the compound (I) of the present invention can be observed, there may be mentioned agricultural and horticultural noxious insects (e.g. Hemiptera (planthoppers, leafhoppers, aphides and whiteflies), Lepidoptera (cabbage armyworms, diamond-back moth, leafroller moths, pyralid moths and contmon cabbage worm), Coleoptera (Tenebrionid beetles, leafbeetles, weevils and scarabs) and Acarina (citrus red mite and two-spotted spider mite of Tetranychidae family and pink citrus rust mite of Eriophyidae family)), hygienically noxious insects (e.g. flies, mosquitoes and cockroaches), noxious insects of stored grains (rust-red flour beetles and bean weevils), and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

(Chemical for controlling noxious organisms)

The agricultural and horticultural chemical for controlling noxious organisms of the present invention has remarkable insecticidal, acaricidal, fungicidal and nematocidal effects, and contains at least one compound (I) as an active ingredient.

The compound (I) can be used singly, but may be preferably used by mixing with a carrier, a surfactant, a dispersant and an auxiliary (for example, prepared as a composition such as a dustable powder, an emulsifiable concentrate, a fine granule, a granule, a wettable powder, an oily suspension and an aerosol) according to a conventional method.

As the carrier, any insecticidally, acaricidally, fungicidally or nematocidally effective carrier may be used, and there may be mentioned, for example, a solid carrier such as talc, bentonite, clay, kaolin, diatomaceous earth, white carbon, vermiculite, calcium hydroxide, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethyl sulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these Examples.

Reference Example 1

(Syntheses of the compounds (II))

(1) Synthesis of 6-(1-chloroethyl)-4,5-dichloropyrimidine (Compound (II-1))

In 750 ml of dichloromethane was dissolved 270 g of 4,5-dichloro- 6-ethylpyrimidine. Under heating at 30 to 35° C. and stirring, chlorine gas was blown into the solution for 2 hours.

Nitrogen gas was blown into the reaction mixture to remove excessive chlorine gas dissolved therein. Then, the solvent was removed under reduced pressure, and the resulting residue was distilled under reduced pressure to obtain 240 g of the title compound as a pale yellow liquid. (2) Synthesis of 4,5-dichloro-6- (1-fluoroethyl)pyrimidine (Compound (II-4))

In 15 ml of dichloromethane was dissolved 2.1 g of 6-(1-hydroxyethyl)-4,5-dichloropyrimidine, and 2.0 g of diethylaminosulfate trifluoride was added dropwise to the solution under ice cooling and stirring. The mixture was further stirred at room temperature for 1 hour to complete the reaction.

To the reaction mixture was added 20 ml of cold water, and the dichloromethane layer was collected by separation, washed with water and then dried over anhydrous sodium sulfate. Then, the solvent was removed under reduced pressure, and the resulting residue was purified by silica gel column chromatography (Wako gel C-200 (trade name, manufactured by Wako Junyaku Co.), eluted by chloroform) to obtain 1.3 g of the title compound as a pale yellow oily liquid.

b.p.: 229° to 231° C. $^1$H-NMR (CDCl$_3$, δ ppm) 1.64 to 1.81 (3H, d-d), 5.84 to 6.19 (1H, d-q), 8.92 (1H, s).

(3) Synthesis of 5-chloro-4-fluoro-6-(1-fluoroethyl)pyrimidine (Compound (II-5))

In 10 ml of N,N-dimethylformamide was dissolved 1.3 g of 4,5-dichloro-6-(1-fluoroethyl)pyrimidine, and 4.0 g of cesium fluoride was added to the solution. The mixture was stirred at room temperature for one hour to complete the reaction.

To the reaction mixture was added 10 ml of cold water, and the separated oily product was extracted with toluene, washed with water and then dried over anhydrous sodium sulfate. Then, the solvent was removed under reduced pressure, and the resulting residue was purified by silica gel column chromatography (Wako gel C-200 (trade name, manufactured by Wako Junyaku Co.), eluted by chloroform) to obtain 1.0 g of the title compound as a pale yellow oily liquid.

b.p.: 192° to 194° C. $^1$H-NMR (CDCl$_3$, δ ppm) 1.66 to 1.82 (3H, d-d), 5.85 to 6.21 (1H, d-q), 8.83 (1H, s).

(4) Synthesis of 6- (1-acetoxyethyl) -4,5-dichloropyrimidine (Compound (II-6))

In 150 ml of N,N-dimethylformamide was dissolved 10.2 g of 6-(1-chloroethyl)-4,5-dichloropyrimidine, and 12.0 g of potassium acetate and 3.0 g of potassium carbonate were added to the solution. The mixture was stirred at about 60° C. for 3 hours.

To the reaction mixture was added 200 ml of water, and the separated oily product was extracted with toluene, washed with water and then dried over anhydrous sodium sulfate. Then, the solvent was removed under reduced pressure, and the resulting residue was purified by silica gel column chromatography (Wako gel C-200 (trade name, manufactured by Wako Junyaku Co.), eluted by toluene:ethyl acetate=10:1) to obtain 5.2 g of the title compound as a pale yellow liquid.

$^1$H-NMR (CDCl$_3$, δ ppm) 1.55 to 1.62 (3H, d), 2.15 (3H, s), 6.00 to 6.12 (1H, q), 8.84 (1H, s).

(5) Synthesis of 4,5-dichloro-6-(1-hydroxyethyl)pyrimidine (Compound (II-7))

In 50 ml of tetrahydrofuran was dissolved 4.0 g of 6-(1-acetoxyethyl)- 4,5-dichloropyrimidine, and 30 ml of a 1N-sodium hydroxide aqueous solution was slowly added dropwise to the solution under stirring. After the dropwise addition, the mixture was further stirred at room temperature for 1 hour to complete the reaction. Then, the reaction mixture was extracted with ethyl acetate, washed with water and dried over anhydrous sodium sulfate, and the solvent was removed under reduced pressure. The resulting oily product was purified by silica gel column chromatography (Wako gel C-200 (trade name, manufactured by Wako Junyaku Co.), eluted by toluene:ethyl acetate=5:1) to obtain 2.8 g of the title compound as a pale yellow liquid.

$^1$H-NMR (CDCl$_3$, δ ppm) 1.47 to 1.52 (3H, d), 3.76 to 3.85 (1H, d), 5.17 to 5.25 (1H, m), 8.88 (1H, s).

(6) Syntheses of other starting compounds (II) in Table 1

According to the same methods as in (1) to (5) described above, the other starting compounds (II) in Table 1 were synthesized.

TABLE 1

(II)

[Structure: pyrimidine ring with Cl, X, N, N positions and H$_3$C-CH(R$^1$)- substituent]

| Compound | X | R$^1$ | Physical Property |
|---|---|---|---|
| II-1 | Cl | Cl | b.p. 110–113° C./7 mmHg |
| II-2 | Br | Br | b.p. 114–116° C./3 mmHg<br>m.p. 60–62° C. |
| II-3 | Cl | Br | b.p. 93–95° C./3 mmHg |
| II-4 | Cl | F | b.p. 229–231° C. |
| II-5 | F | F | b.p. 192–194° C. |
| II-6 | Cl | $-\text{OCCH}_3$ (O=) | $n_D^{17.7}$ 1.5222 |
| II-7 | Cl | OH | $n_D^{19.3}$ 1.5540 |

Example 1

(Syntheses of the compounds (I))

By using the compounds (II) obtained in Reference example 1, the desired compounds (I) were synthesized.

(1) Synthesis of 5-chloro-6-(1-fluoroethyl)-4-(2-phenylethylamino)pyrimidine (Compound No. 1)

In 30 ml of toluene were dissolved 1.2 g of 2-phenylethylamine and 1.2 g of triethylamine, and 2.0 g of 4,5-dichloro-6-(1-fluoroethyl)pyrimidine was added to the solution. The mixture was refluxed under heating for 4 hours.

After completion of the reaction, water was added to the reaction mixture. The mixture was extracted with toluene, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=10:1) to obtain 2.3 g of the title compound as colorless powdery crystals.

$^1$H-NMR (CDCl$_3$, δ ppm) 1.59 to 1.72 (3H, d-d), 2.84 to 2.95 (2H, t), 3.71 to 3.79 (2H, q), 5.48 to 5.60 (1H, m), 5.73 to 6.01 (1H, m), 7.11 to 7.36 (5H, m), 8.52 (1H, s).

(2) Synthesis of 5-chloro-6-(1-hydroxyethyl)-4-(2-phenylethylamino) pyrimidine (Compound No. 2)

In 30 ml of toluene were dissolved 1.2 g of 2-phenylethylamine and 1.2 g of triethylamine, and 2.0 g of 4,5-dichloro-6-(1-hydroxyethyl)pyrimidine was added to the solution. The mixture was refluxed under heating for 3 hours.

After completion of the reaction, water was added to the reaction mixture. The mixture was extracted with toluene, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=5:1) to obtain 2.2 g of the title compound as colorless powdery crystals.

(3) Synthesis of 5-chloro-6-(1-chloroethyl)-4-[2-( 4-methylphenyl)ethylamino]pyrimidine (Compound No. 3).

In 100 ml of toluene were dissolved 4.1 g of 2-(4-methylphenyl)ethylamine and 5.0 g of triethylamine, and 6.3 g of 4,5-dichloro-6-(1-chloroethyl)pyrimidine was added to the solution. The mixture was refluxed under heating for 3 hours.

After completion of the reaction, water was added to the reaction mixture. The mixture was extracted with toluene, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=10:1) to obtain 8.4 g of the title compound as colorless powdery crystals.

Synthesis of 6-(1-acetoxyethyl)-5-chloro-4-[2-( 4-methylphenyl)ethylamino]pyrimidine (Compound No. 4)

In 50 ml of N,N-dimethylformamide was dissolved 3.5 g of Compound No. 3 obtained in the above (3), and 1.4 g of potassium acetate and 1.6 g of potassium carbonate were added to the solution. The mixture was stirred at about 60° C. for 4 hours.

After completion of the reaction, water was added to the reaction mixture. The mixture was extracted with ethyl acetate, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=4:1) to obtain 2.0 g of the title compound as a colorless oily liquid.

(5) Synthesis of 5-chloro-6-(1-hydroxyethyl)-4-[2-( 4-methylphenyl)ethylamino]pyrimidine (Compound No. 5)

In 25 ml of ethanol was dissolved 2.3 g of Compound No. 4 obtained in the above (4), and 13 ml of a 1N-sodium hydroxide aqueous solution was added to the solution. The mixture was stirred under heating at about 60° C. for 1 hour.

After completion of the reaction, water was added to the reaction mixture. The mixture was extracted with ethyl acetate, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=4:1) to obtain 2.0 g of the title compound as a colorless oily liquid.

(6) Synthesis of 5-chloro-6-(1-fluoroethyl)-4-[2-( 4-methylphenyl)ethylamino]pyrimidine (Compound No. 6)

In 30 ml of methylene chloride was dissolved 1.5 g of Compound No. 5 obtained in the above (5), and 0.8 g of diethylaminosulfate trifluoride (DAST) was added dropwise to the solution under ice cooling and stirring. The mixture was stirred at room temperature for 1 hour.

After completion of the reaction, under ice cooling and stirring, water was slowly added to the reaction mixture to separate the organic solvent layer. The organic solvent layer was washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene:ethyl acetate=10:1) to obtain 1.0 g of the title compound as a pale yellow oily liquid.

(7) Synthesis of 5-chloro-6-(1-fluoroethyl)-4-[2-( 4-methoxyphenyl)ethylamino]pyrimidine (Compound No. 10)

In 30 ml of N,N-dimethylformamide was dissolved 1.5 g of 5-chloro-6-(1-chloroethyl)-4-[2-(4-methoxyphenyl)ethylamino]pyrimidine, and 1.5 g of cesium fluoride was added to the solution. The mixture was stirred at 120° to 140° C. for 12 hours.

After completion of the reaction, water was added to the reaction mixture. The mixture was extracted with ethyl acetate, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co. ), eluted by toluene:ethyl acetate=9: 1) to obtain 0.5 g of the title compound as colorless powdery crystals.

(8) Synthesis of 5-chloro-4-{2-[4-(4-chlorobenzoyl)phenyl]ethylamino}-6-(1-fluoroethyl)pyrimidine (Compound No. 25)

In 20 ml of methylene chloride was dissolved 0.8 g of 5-chloro-4-{2-[4-(4-chlorobenzoyl)phenyl]ethylamino}-6-(1-hydroxyethyl)pyrimidine, and 0.4 g of DAST was added dropwise to the solution under ice cooling and stirring. The mixture was stirred at room temperature for 1 hour.

After completion of the reaction, under ice cooling and stirring, water was slowly added to the reaction mixture to separate the organic solvent layer. The organic solvent layer was washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene- :ethyl acetate=10:1) to obtain 0.4 g of the title compound as a colorless oily liquid.

$^1$H-NMR (CDCl$_3$, δ ppm) 1.57 to 1.72 (3H, d-d), 3.02 to 3.07 (2H, t), 3.79 to 3.89 (2H, m), 5.51 to 5.65 (1H, m), 5.76 to 6.01 (1H, d-q), 7.31 to 7.39 (2H, d), 7.43 to 7.49 (2H, d), 7.72 to 7.77 (4H, m), 8.56 (1H, s)

(9) Synthesis of 5-chloro-6-(1-chloroethyl)-4-{2-[4-(4-methylbenzoyl)phenyl]ethylamino}pyrimidine (Compound No. 26)

In 20 ml of toluene were dissolved 4.0 g of 2-[4-(4-methylbenzoyl)phenyl]ethylamine and 7.0 g of triethylamine, and 4.0 g of 4,5-dichloro-6-(1-chloroethyl)pyrimidine was added to the solution. The mixture was stirred at 60° C. for 3 hours.

After completion of the reaction, water was added to the reaction mixture. The mixture was extracted with toluene, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene-:ethyl acetate=10:1) to obtain 2.0 g of the title compound as colorless crystals.

$^1$H-NMR (CDCl$_3$, δ ppm) 1.82 to 1.85 (3H, d), 2.45 (3H, s), 2.99 to 3.08 (2H, t), 3.80 to 3.88 (2H, m), 5.36 to 5.43 (1H, q), 5.56 to 5.68 (1H, m), 7.28 to 7.38 (4H, d-d), 7.69 to 7.80 (4H, d-d), 8.57 (1H, s).

(10) Synthesis of 6-(1-acetoxyethyl)-5-chloro-4-{2-[4-(4-methylbenzoyl)phenyl]ethylamino}pyrimidine (Compound No. 27)

In 30 ml of N,N-dimethylformamide was dissolved 1.5 g of Compound No. 26 obtained in the above (9), and 0.7 g of potassium acetate was added to the solution. The mixture was stirred at about 60° C. for 4 hours.

After completion of the reaction, water was added to the reaction mixture. The mixture was extracted with ethyl acetate, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene-:ethyl acetate=10:1) to obtain 1.3 g of the title compound as a colorless oily liquid.

$^1$H-NMR (CDCl$_3$, δ ppm) 1.53 to 1.55 (3H, d), 2.13 (3H, s), 2.44 (3H, s), 3.00 to 3.05 (2H, t), 3.79 to 3.84 (2H, m), 5.54 to 5.56 (1H, m), 5.97 to 6.04 (1H, q), 7.27 to 7.36 (4H, d-d), 7.69 to 7.78 (4H, d-d), 8.52 (1H, s).

(11) Synthesis of 5-chloro-6-(1-hydroxyethyl)-4-{2-[4-(4-methylbenzoyl)phenyl]ethylamino}pyrimidine (Compound No. 28)

In 50 ml of N,N-dimethylformamide was dissolved 1.0 g of Compound No. 27 obtained in the above (10), and 20 ml of a 1N-sodium hydroxide aqueous solution was added to the solution. The mixture was stirred at about 60° C. for 1 hour.

After completion of the reaction, water was added to the reaction mixture. The mixture was extracted with ethyl acetate, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene-:ethyl acetate=10:1) to obtain 0.7 g of the title compound as colorless crystals.

$^1$H-NMR (CDCl$_3$δ ppm) 1.41 to 1.43 (3H, d), 2.44 (3H, s), 2.95 to 3.06 (2H, t), 3.80 to 3.89 (2H, m), 4.16 to 4.19 (1H, m), 4.96 to 5.02 (1H, m), 5.53 to 5.59 (1H, m), 7.27 to 7.35 (4H, d-d), 7.69 to 7.77 (4H, d-d), 8.50 (1H, s) .

(12) Synthesis of 5-chloro-6-(1-fluoroethyl)-4-{2-[4-(4-methylbenzoyl)phenyl]ethylamino}pyrimidine (Compound No. 29)

In 20 ml of methylene chloride was dissolved 0.38 g of Compound No. 28 obtained in the above (11), and 0.18 g of DAST was added dropwise to the solution under ice cooling and stirring. The mixture was stirred at room temperature for 1 hour.

After completion of the reaction, under ice cooling and stirring, water was slowly added to the reaction mixture to separate the organic solvent layer. The organic solvent layer was washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene-:ethyl acetate=10:1) to obtain 0.2 g of the title compound as colorless crystals.

$^1$H-NMR (CDCl$_3$δ ppm) 1.61 to 1.72 (3H, d-d), 2.44 (3H, s), 3.01 to 3.06 (2H, t), 3.81 to 3.89 (2H, m), 5.57 to 5.64 (1H, m), 5.76 to 6.01 (1H, d-q), 7.27 to 7.35 (4H, d-d), 7.69 to 7.78 (4H, d-d), 8.56 (1H, s).

(13) Synthesis of 5-chloro-6-(1-fluoroethyl)-4-{2-[ 4-(trifluoromethyl)phenyl]ethylamino}pyrimidine (Compound No. 33)

In 20 ml of toluene were dissolved 1.9 g of 2-[4-(trifluoromethyl)phenyl]ethylamine and 3 g of triethylamine, and 2.0 g of 4,5-dichloro-6-(1-fluoroethyl)pyrimidine obtained in Reference example 1 was added to the solution. The mixture was stirred under heating at about 60° C. for 4 hours.

After completion of the reaction, water was added to the reaction mixture and the mixture was extracted with toluene. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 2.7 g of the title compound as colorless crystals.

$^1$H-NMR (CDCl$_3$δ ppm) 1.60 to 1.72 (3H, d-d), 2.99 to 3.04 (2H, t), 3.78 to 3.86 (2H, m), 5.48 to 5.62 (1H, m), 5.76 to 6.01 (1H, d-q), 7.33 to 7.36 (2H, d), 7.57 to 7.60 (2H, d), 8.56 (1H, s).

(14) Synthesis of 5-chloro-6-(1-fluoroethyl)-4-{2-[ 4-(trifluoromethoxy)phenyl]ethylamino}pyrimidine (Compound No. 34)

In 20 ml of toluene were dissolved 2.05 g of 2-[4-(trifluoromethoxy)phenyl]ethylamine and 3 g of triethylamine, and 2.0 g of 4,5-dichloro-6-(1-fluoroethyl)pyrimidine obtained in Reference example 1 was added to the solution. The mixture was stirred under heating at about 60° C. for 4 hours.

After completion of the reaction, water was added to the reaction mixture and the mixture was extracted with toluene. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 2.6 g of the title compound as pale yellow crystals.

$^1$H-NMR (CDCl$_3$ δ ppm) 1.62 to 1.73 (3H, d-d), 2.92 to 3.01 (2H, t), 3.76 to 3.85 (2H, m), 5.46 to 5.62 (1H, m), 5.78 to 6.04 (1H, d-q), 7.11 to 7.20 (2H, d), 7.22 to 7.28 (2H, d), 8.59 (1H, s).

(15) Synthesis of 5-chloro-6-(1-chloroethyl)-4-{2-[ 4-(2,2, 2-trifluoroethoxy)phenyl]ethylamino}pyrimidine (Compound No. 48)

In 100 ml of toluene were dissolved 5.5 g of 2-[4-(2,2, 2-trifluoroethoxy)phenyl]ethylamine and 6 g of triethylamine, and 6.4 g of 4,5-dichloro-6-(1-chloroethyl)pyrimidine obtained in Reference example 1 was added to the solution. The mixture was stirred under heating at about 60° C. for 4 hours.

After completion of the reaction, water was added to the reaction mixture and the mixture was extracted with toluene. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 7.5 g of the title compound as colorless crystals.

$^1$H-NMR (CDCl$_3$, δ ppm) 1.82 to 1.91 (3H, d), 2.88 to 2.98 (2H, t), 3.72 to 3.80 (2H, m), 4.30 to 4.39 (2H, q), 5.36 to 5.43 (1H, q), 5.55 to 5.60 (1H, m), 6.89 to 6.93 (2H, d), 7.16 to 7.26 (2H, d), 8.54 (1H, s).

(16) Synthesis of 6-(1-acetoxyethyl)-5-chloro-4-{2-[ 4-(2,2, 2-trifluoroethoxy)phenyl]ethylamino}pyrimidine (Compound No. 49)

In 30 ml of N,N-dimethylformamide was dissolved 3.8 g of the Compound No. 48 obtained in the above (15), and 1.9 g of potassium acetate and 2.6 g of potassium carbonate were added to the solution. The mixture was stirred under heating at about 60° C. for 4 hours.

After completion of the reaction, water was added to the reaction mixture and the mixture was extracted with ethyl acetate. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 3.8 g of the title compound as colorless oily liquid.

$^1$H-NMR (CDCl$_3$, δ ppm) 1.52 to 1.55 (3H, d), 2.13 (3H, s), 2.86 to 2.91 (2H, t), 3.72 to 3.75 (2H, m), 4.29 to 4.39 (2H, q), 5.45 to 5.55 (1H, m), 5.96 to 6.01 (1H, q), 6.89 to 6.92 (2H, d), 7.16 to 7.19 (2H, d), 8.49 (1H, s).

(17) Synthesis of 5-chloro-6-(1-hydroxyethyl)-4-{2-[ 4-(2, 2,2-trifluoroethoxy)phenyl]ethylamino}pyrimidine (Compound No. 50)

In 40 ml of ethanol was dissolved 3.6 g of the Compound No. 49 obtained in the above (16), and 20 ml of a 1N sodium hydroxide aqueous solution was added to the solution. The mixture was stirred under heating at about 60° C. for one hour.

After completion of the reaction, water was added to the reaction mixture and the mixture was extracted with ethyl acetate. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=4:1 to obtain 3.1 g of the title compound as colorless crystals.

$^1$H-NMR (CDCl$_3$, δ ppm) 1.40 to 1.43 (3H, d), 2.88 to 2.93 (2H, t), 3.72 to 3.83 (2H, m), 4.13 to 4.16 (1H, m), 4.29 to 4.39 (2H, q), 4.95 to 5.01 (1H, m), 5.42 to 5.55 (1H, m), 6.89 to 6.94 (2H, d), 7.16 to 7.19 (2H, d), 8.48 (1H, s).

(18) Synthesis of 5-chloro-6-(1-fluoroethyl)-4-{2-[ 4-(2,2,2 -trifluoroethoxy)phenyl]ethylamino}pyrimidine (Compound No. 51)

In 30 ml of methylene chloride was dissolved 2.8 g of the Compound No. 50 obtained in the above (17), and 1.4 g of DAST was added dropwise to the solution under cooling and stirring. The mixture was stirred at room temperature for one hour.

After completion of the reaction, under ice cooling and stirring, water was slowly added to the reaction mixture. The mixture was extracted with methylene chloride, and the organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 2.2 g of the title compound as colorless crystals.

$^1$H-NMR (CDCl$_3$, δ ppm) 1.60 to 1.75 (3H, d-d), 2.88 to 2.93 (2H, t), 3.72 to 3.82 (2H, m), 4.30 to 4.39 (2H, q), 5.44 to 5.60 (1H, m), 5.75 to 6.00 (1H, d-q), 6.88 to 6.92 (2H, d), 7.15 to 7.19 (2H, d), 8.55 (1H, s).

(19) Synthesis of 5-chloro-6-(1-methylthio)-4-{2-[4-( 4-methylthiobenzoyl)phenyl]ethylamino}pyrimidine (Compound No. 89)

In 20 ml of tetrahydrofuran was dissolved 1.3 g of 5-chloro- 6-(1-chloroethyl)-4-{2-[4-(4-methylthiobenzoyl)phenyl]ethylamino}pyrimidine, and 1.4 g of a 15% methyl mercaptan sodium salt aqueous solution was added dropwise to the solution. After completion of the dropwise addition, the mixture was stirred under heating at about 60° C for 2 hours to complete the reaction.

After completion of the reaction, water was added to the reaction mixture and the mixture was extracted with ethyl acetate. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene:ethyl acetate=10:1) to obtain 1.1 g of the title compound as colorless crystals.

$^1$H-NMR (CDCl$_3$ δ ppm) 1.59 to 1.62 (3H, d), 2.60 (3H, s), 2.53 (3H, s), 3.00 to 3.06 (2H, t), 3.79 to 3.86 (2H, m), 4.28 to 4.36 (1H, q), 5.51 to 5.60 (1H, m), 7.27 to 7.35 (4H, m), 7.72 to 7.74 (2H, d), 7.75 to 7.76 (2H, d), 8.52 (1H, s).

(20) Synthesis of 5-chloro-6-(1-fluoroethyl)-4-{2-[ 4-(2,2, 2-trifluoroethoxy)3-methylphenyl]ethylamino} -pyrimidine (Compound No. 93)

In 40 ml of toluene were dissolved 2.3 g of 2-[4-(2,2,2-trifluoroethoxy)3-methylphenyl]ethylamine and 3 g of triethylamine, and 2.0 g of 4,5-dichloro-6-(1-fluoroethyl)pyrimidine obtained in Reference example 1 was added to the solution. The mixture was stirred under heating at about 60° C. for 4 hours.

After completion of the reaction, water was added to the reaction mixture and the mixture was extracted with toluene. The organic layer was washed with water and dried over anhydrous sodium sulfate. Then, the solvent was removed under reduced pressure.

The obtained residue was purified by silica gel column chromatography (Wako gel C-200 (trade name, manufactured by Wako Junyaku Co.), eluted by toluene: ethyl acetate=10:1) to obtain 3.2 g of the title compound as colorless crystals.

$^1$H-NMR (CDCl$_3$, δ ppm) 1.60 to 1.71 (3H, d-d), 2.28 (3H, s), 2.83 to 2.88 (2H, t), 3.71 to 3.79 (2H, m), 4.29 to 4.38 (2H, q), 5.48 to 5.62 (1H, m), 5.72 to 6.00 (1H, d-q), 6.73 to 7.04 (3H, m), 8.54 (1H, s).

(21) Syntheses of other compounds (I) in Table 2

According to the methods described in the above (1) to (20), the other compounds (I) in Table 2 were synthesized.

The compounds synthesized as described above are shown in Table 2.

TABLE 2

| Compound | R$^1$ | (R$^2$)$_n$ | Physical property |
|---|---|---|---|
| 1 | F | H | m.p. 78~80° C. |
| 2 | OH | H | m.p. 70~72° C. |
| 3 | Cl | 4-CH$_3$ | m.p. 101~103° C. |
| 4 | —OC(O)CH$_3$ | 4-CH$_3$ | n$_D^{19.6}$ 1.5574 |
| 5 | OH | 4-CH$_3$ | m.p. 87~89° C. |
| 6 | F | 4-CH$_3$ | m.p. 101~103° C. |
| 7 | Cl | 4-OCH$_3$ | m.p. 86~87° C. |
| 8 | —OC(O)CH$_3$ | 4-OCH$_3$ | n$_D^{19.6}$ 1.5624 |
| 9 | OH | 4-OCH$_3$ | n$_D^{19.6}$ 1.5768 |
| 10 | F | 4-OCH$_3$ | m.p. 58~59° C. |
| 11 | Cl | 4-F | m.p. 115~117° C. |
| 12 | —OC(O)CH$_3$ | 4-F | m.p. 104~106° C. |
| 13 | OH | 4-F | m.p. 118~119° C. |
| 14 | F | 4-F | m.p. 93~94° C. |
| 15 | F | 4-Cl | m.p. 106~108° C. |
| 16 | Cl | 4-CO-C$_6$H$_4$-F | m.p. 119~122° C. |
| 17 | F | 4-CO-C$_6$H$_4$-F | |
| 18 | Cl | 4-CO-C$_6$H$_5$ | m.p. 132~134° C. |
| 19 | —OC(O)CH$_3$ | 4-CO-C$_6$H$_5$ | n$_D^{17.0}$ 1.5962 |
| 20 | OH | 4-CO-C$_6$H$_5$ | m.p. 124~126° C. |

TABLE 2-continued
(1)
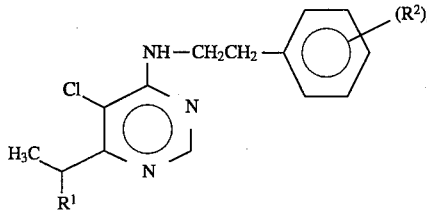
| Compound | R¹ | (R²)ₙ | Physical property |
|---|---|---|---|
| 21 | F | 4-CO—⌬ | m.p. 105~107° C. |
| 22 | Cl | 4-CO—⌬—Cl | m.p. 115~118° C. |
| 23 | —OC(O)CH₃ | 4-CO—⌬—Cl | Viscous |
| 24 | OH | 4-CO—⌬—Cl | m.p. 132~134° C. |
| 25 | F | 4-CO—⌬—Cl | $n_D^{17.2}$ 1.6172 |
| 26 | Cl | 4-CO—⌬—CH₃ | m.p. 140~143° C. |
| 27 | —OC(O)CH₃ | 4-CO—⌬—CH₃ | $n_D^{15.0}$ 1.5874 |
| 28 | OH | 4-CO—⌬—CH₃ | m.p. 109~112° C. |
| 29 | F | 4-CO—⌬—CH₃ | m.p. 86~88° C. |
| 30 | F | 4-CO—⌬(Cl)(Cl) | |
| 31 | F | 4-CO—⌬—OCH₃ | |
| 32 | F | 4-CO—⌬—CF₃ | |

TABLE 2-continued

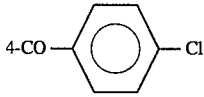 (1)

| Compound | R¹ | (R²)ₙ | Physical property |
|---|---|---|---|
| 33 | F | 4-CF₃ | m.p. 69–70° C. |
| 34 | F | 4-OCF₃ | m.p. 95–97° C. |
| 35 | Cl | 4-OCHF₂ | |
| 36 | —OCCH₃ (O=) | 4-OCHF₂ | |
| 37 | OH | 4-OCHF₂ | |
| 38 | F | 4-OCHF₂ | $n_D^{20.0}$ 1.5560 |
| 39 | —OCH₃ | 4-CO—C₆H₄—Cl | m.p. 86–88° C. |
| 40 | —SCH₃ | 4-CO—C₆H₄—Cl | m.p. 100–102° C. |
| 41 | Cl | 4-OH | m.p. 156–157° C. |
| 42 | Cl | 4-CCF₃ (O=) | m.p. 69–72° C. |
| 43 | F | 4-CCF₃ (O=) | m.p. 96–97° C. |
| 44 | Cl | 4-OSO₂CH₃ | $n_D^{19.6}$ 1.5734 |
| 45 | —OCCH₃ (O=) | 4-OSO₂CH₃ | $n_D^{19.5}$ 1.5482 |
| 46 | OH | 4-OSO₂CH₃ | $n_D^{20.2}$ 1.5659 |
| 47 | F | 4-OSO₂CH₃ | $n_D^{19.9}$ 1.5668 |
| 48 | Cl | 4-OCH₂CF₃ | m.p. 54–56° C. |
| 49 | —OCCH₃ (O=) | 4-OCH₂CF₃ | $n_D^{19.8}$ 1.5306 |
| 50 | OH | 4-OCH₂CF₃ | m.p. 43–45° C. |
| 51 | F | 4-OCH₂CF₃ | m.p. 85–87° C. |
| 52 | —OCH₃ | 4-OCH₂CF₃ | $n_D^{26.0}$ 1.5326 |
| 53 | —OCOCH₂—C₆H₅ (O=) | 4-OCH₂CF₃ | $n_D^{19.7}$ 1.5502 |
| 54 | —OCO-t-C₄H₉ (O=) | 4-OCH₂CF₃ | m.p. 127–129° C. |
| 55 | Cl | 4-OSO₂CF₃ | m.p. 80–82° C. |
| 56 | —OCCH₃ (O=) | 4-OSO₂CF₃ | $n_D^{20.9}$ 1.5108 |
| 57 | OH | 4-OSO₂CF₃ | |
| 58 | F | 4-OSO₂CF₃ | m.p. 67–69° C. |

TABLE 2-continued $$\text{(1)}$$

(Structure: pyrimidine with Cl, NH-CH$_2$CH$_2$-phenyl(R$^2$)$_n$, and H$_3$C-CH(R$^1$)- substituent)

| Compound | R$^1$ | (R$^2$)$_n$ | Physical property |
|---|---|---|---|
| 59 | —OSO$_2$CH$_3$ | 4-CO—(C$_6$H$_4$)—Cl | Viscous |
| 60 | —OSi(CH$_3$)$_3$ | 4-CO—(C$_6$H$_4$)—Cl | n$_D^{20.9}$ 1.5864 |
| 61 | —OCH$_2$COCH$_3$ | 4-CO—(C$_6$H$_4$)—Cl | n$_D^{22.0}$ 1.5966 |
| 62 | Cl | 4-CF$_3$ | m.p. 92~94° C. |
| 63 | —OCCH$_3$ (O=) | 4-CF$_3$ | n$_D^{22.3}$ 1.5282 |
| 64 | OH | 4-CF$_3$ | n$_D^{20.0}$ 1.5438 |
| 65 | Cl | 4-OCF$_3$ | n$_D^{19.5}$ 1.5408 |
| 66 | —OCCH$_3$ (O=) | 4-OCF$_3$ | m.p. 59~61° C. |
| 67 | OH | 4-OCF$_3$ | n$_D^{20.8}$ 1.5380 |
| 68 | F | 4-C(=N-OCH$_3$)—(C$_6$H$_4$)—Cl | n$_D^{18.8}$ 1.5984 |
| 69 | F | 4-(1,3-dioxolan-2-yl with methyl)—(C$_6$H$_4$)—Cl | m.p. 108~109° C. |
| 70 | F | 4-CHF—(C$_6$H$_4$)—Cl | m.p. 123~126° C. |
| 71 | F | 4-OCF$_2$CHFCF$_3$ | n$_D^{19.8}$ 1.5020 |
| 72 | —OCF$_2$CHFCF$_3$ | 4-OCF$_2$CHFCF$_3$ | n$_D^{19.5}$ 1.4688 |
| 73 | F | 4-OCHFCHF$_2$ | n$_D^{19.8}$ 1.5484 |
| 74 | F | 4-O—(C$_6$F$_5$) | m.p. 90.0~91.5° C. |
| 75 | F | 4-OCF$_2$CHFCl | m.p. 68~70° C. |
| 76 | —OCF$_2$CHFCl | 4-OCF$_2$CHFCl | n$_D^{19.9}$ 1.5130 |

TABLE 2-continued (1)

structure: 5-Cl, 6-CH(R¹)CH₃, 4-NHCH₂CH₂-C₆H₄(R²)ₙ pyrimidine

| Compound | R¹ | (R²)ₙ | Physical property |
|---|---|---|---|
| 77 | F | 4-OCH=CH—CH=CF₂ | $n_D^{19.8}$ 1.5638 |
| 78 | F | 4-OC₂H₅ | m.p. 104~106° C. |
| 79 | F | 4-OCH₂CH=CH₂ | m.p. 88~89° C. |
| 80 | F | 4-OCH₂Si(CH₃)₃ | m.p. 102~104° C. |
| 81 | F | 4-SCH₃ | m.p. 70~71° C. |
| 82 | F | 4-OH | m.p. 172~174° C. |
| 83 | F | 4-O—C₆H₄—CF₃ | $n_D^{20.3}$ 1.5436 |
| 84 | F | 4-t-C₄H₉ | m.p. 86~88° C. |
| 85 | F | 4-SO₂CH₃ | m.p. 111~112° C. |
| 86 | F | 4-SOCH₃ | Viscous |
| 87 | F | 4-O—(3-Cl, 5-CF₃-pyridin-2-yl) | $n_D^{19.7}$ 1.5636 |
| 88 | F | 4-SOCH₂F | m.p. 105~107° C. |
| 89 | —SCH₃ | 4-CO—C₆H₄—SCH₃ | m.p. 100~102° C. |
| 90 | Cl | 4-C(=N—N(CH₃)₂)—C₆H₄—Cl  Isomer-1 | Viscous |
| 91 | Cl | 4-C(=N—N(CH₃)₂)—C₆H₄—Cl  Isomer-2 | Viscous |
| 92 | OH | 4-CH(OH)—C₆H₄—Cl | m.p. 51~54° C. |
| 93 | F | 3-CH₃, 4-OCH₂CF₃ | $n_D^{19.5}$ 1.5302 |
| 94 | F | 4-CO—C₆H₄—CF₃ | |
| 95 | F | 4-O-n-C₄H₉ | |
| 96 | F | 4-OCH₂CH₂CF=CF₂ | |
| 97 | F | 4-O-t-C₄H₉ | |
| 98 | F | 4-SCH₂CF₃ | |
| 99 | F | 4-CO—CH₃ | |
| 100 | F | 4-O—(5-Cl-pyridin-2-yl) | |

TABLE 2-continued

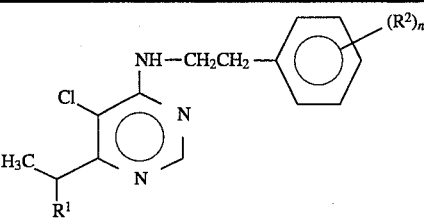 (1)

| Compound | R¹ | (R²)ₙ | Physical property |
|---|---|---|---|
| 101 | F | 4-O-(pyridyl)-CF₃ | |
| 102 | F | 4-O-(pyridyl)-Cl | |
| 103 | F | 4-O-(pyridyl)-CF₃ | |
| 104 | F | 4-O-(phenyl) | |
| 105 | F | 4-O-(phenyl)-Cl | |
| 106 | F | 4-O-(phenyl)-F | |
| 107 | F | 4-OCH₂C≡C | |
| 108 | Cl | 4-NO₂ | m.p. 124~125° C. |
| 109 | —OCCH₃ (O=) | 4-NO₂ | m.p. 140~141° C. |
| 110 | OH | 4-NO₂ | m.p. 107~109° C. |
| 111 | F | 4-NO₂ | m.p. 121~123° C. |
| 112 | Cl | 4-Cl | m.p. 112~113° C. |
| 113 | —OCCH₃ (O=) | 4-Cl | m.p. 83~85° C. |
| 114 | OH | 4-Cl | m.p. 94~95° C. |

Physical properties of some compounds are shown in Table 3 below.

TABLE 3

$^1$H-NMR (CDCl$_3$, δ ppm)

(Compound No. 59)

1.68~1.73 (3H, d), 3.02 (3H, s),
3.05~3.07 (2H, m), 3.81~3.88 (2H, m),

TABLE 3-continued $^1$H-NMR (CDCl$_3$, δ ppm)

5.58~5.63 (1H, m), 6.04~6.11 (1H, m),
7.34~7.37 (2H, d), 7.45~7.48 (2H, d),
7.72~7.77 (4H, m), 8.56 (1H, s)

(Compound No. 86)

1.60~1.73 (3H, d-d), 2.73 (3H, s),
3.00~3.05 (2H, m), 3.81~3.84 (2H, m),

TABLE 3-continued

| $^1$H-NMR (CDCl$_3$, δ ppm) |
|---|
| 5.48~5.65 (1H, m), 5.81~5.96 (1H, d-q), 7.38~7.41 (2H, d), 7.60~7.63 (2H, d), 8.56 (1H, s) (Compound No. 90) |
| 1.82~1.85 (3H, d), 2.54 (6H, s), 2.97~3.02 (2H, m), 3.80~3.88 (2H, m), 5.35~5.43 (1H, m), 5.49~5.68 (1H, m), 7.18~7.76 (8H, m), 8.56 (1H, s) (Compound No. 91) |
| 1.81~1.85 (3H, d), 2.54 (6H, s) 3.01~3.06 (2H, m), 3.80~3.87 (2H, m), 5.37~5.41 (1H, m), 5.57~5.68 (1H, m), 7.18~7.76 (8H, m), 8.56 (1H, s) |

Example 2

(Preparation of formulations)

(1) Preparation of granule

Five parts by weight of Compound 1 was uniformly mixed with 35 parts by weight of bentonite, 57 parts by weight of talc, 1 part by weight of Neopelex powder (trade name, produced by Kao K. K.) and 2 parts by weight of sodium lignosulfonate, and then, the mixture was kneaded with addition of a small amount of water, followed by granulation and drying, to obtain a granule.

(2) Preparation of wettable powder

Ten parts by weight of Compound 1 was uniformly mixed with 67.5 parts by weight of kaolin, 20 parts by weight of white carbon, 2 parts by weight of Neopelex powder (trade name, produced by Kao K. K.) and 0.5 part by weight of Demol (trade name, produced by Kao K. K.), and then the mixture was pulverized to obtain a wettable powder.

(3) Preparation of emulsifiable concentrate

Twenty parts by weight of Compound 1 was uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dustable powder

Five parts by weight of Compound I was uniformly mixed with 50 parts by weight of talc and 45 parts by weight of kaolin to obtain a dustable powder.

Example 3

(tests of effects)

(1) Test of effect on diamond-back moth

The respective wettable powders of the compounds (I) shown in Table 2 prepared as in Example 2 were diluted to 300 ppm with water containing a surfactant (0.01%). In these respective chemicals, cabbage leaves (5×5 cm) were dipped for 30 seconds, respectively, and each leaf was put into the respective plastic cups and air-dried.

Subsequently, 10 diamond-back moths (3th instar larvae) were placed in the respective cups. The cups were closed and left to stand in a thermostat chamber at 25° C. After 2 days, insecticidal rate was determined by counting living and dead insects in the respective cups.

The insecticidal effect was evaluated by using 4 ranks depending on the range of insecticidal rate (A: 100% B: less than 100 to 80%, C: less than 80 to 60% and D: less than 60%).

For comparison, Comparative compounds 1 to 3 described in Japanese Provisional Patent Publication No. 36666/1984 and Comparative compounds 4 to 7 described in Japanese Provisional Patent Publication No. 201999/1993 shown in Table 4 were evaluated in the same manner as in the compounds (1).

TABLE 4

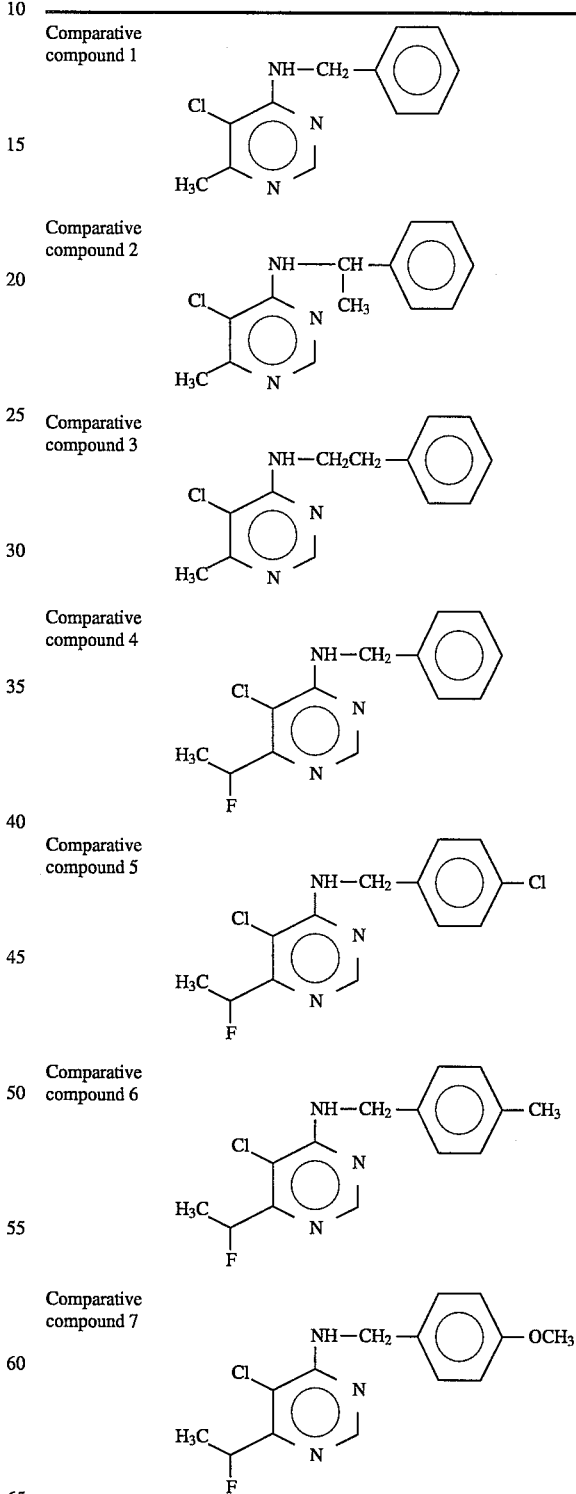

The results are shown in Table 5.

TABLE 5

Test of effect on diamond-back moth

| Compound | Effect |
|---|---|
| 1 | A |
| 6 | A |
| 10 | A |
| 14 | A |
| 15 | A |
| 16 | A |
| 18 | B |
| 19 | B |
| 20 | B |
| 21 | A |
| 23 | A |
| 24 | A |
| 25 | A |
| 27 | A |
| 28 | A |
| 29 | A |
| 33 | A |
| 34 | A |
| 38 | A |
| 40 | A |
| 43 | A |
| 47 | A |
| 48 | A |
| 50 | A |
| 51 | A |
| 52 | A |
| 53 | A |
| 54 | A |
| 56 | A |
| 58 | A |
| 59 | A |
| 60 | A |
| 63 | A |
| 67 | A |
| 68 | A |
| 69 | A |
| 70 | A |
| 71 | A |
| 72 | B |
| 73 | A |
| 74 | A |
| 75 | A |
| 76 | A |
| 77 | A |
| 78 | A |
| 79 | A |
| 80 | A |
| 81 | A |
| 83 | A |
| 84 | A |
| 87 | A |
| 88 | A |
| 90 | A |
| 91 | A |
| 92 | A |
| 93 | A |
| 111 | A |
| Comparative compound 1 | D |
| Comparative compound 2 | D |
| Comparative compound 3 | D |
| Comparative compound 4 | D |
| Comparative compound 5 | D |
| Comparative compound 6 | D |
| Comparative compound 7 | D |

(2) Test of effect on brown rice planthopper

The respective wettable powders of the compounds (1) shown in Table 2 prepared as in Example 2 were diluted to 300 ppm with water containing a surfactant (0.01%). In these respective chemicals, young seedlings of rice were dipped for 30 seconds, respectively, air-dried and put into the respective glass cylinders.

Subsequently, 10 brown rice planthoppers (4th instar nymphs) were placed in the respective glass cylinders. The cylinders were closed with porous caps and left to stand in a thermostat chamber at 25° C. After 4 days, insecticidal rate was determined by counting living and dead insects in the respective glass cylinders.

The evaluation results of the insecticidal effect of the present compounds and the comparative compounds described in the above (1) are shown in Table 6 according to the 4 rank evaluation method.

TABLE 6

Test of effect on brown rice planthopper

| Compound | Effect |
|---|---|
| 1 | A |
| 14 | A |
| 15 | A |
| 21 | A |
| 23 | B |
| 25 | A |
| 29 | A |
| 33 | A |
| 34 | A |
| 38 | A |
| 43 | A |
| 47 | B |
| 51 | A |
| 54 | B |
| 58 | A |
| 69 | A |
| 70 | A |
| 71 | A |
| 73 | A |
| 75 | A |
| 77 | B |
| 78 | A |
| 79 | A |
| 83 | A |
| 84 | A |
| 87 | A |
| 90 | A |
| 91 | A |
| 93 | A |
| 111 | A |
| Comparative compound 1 | D |
| Comparative compound 2 | D |
| Comparative compound 3 | D |
| Comparative compound 4 | D |
| Comparative compound 5 | D |
| Comparative compound 6 | D |
| Comparative compound 7 | D |

(3) Test of effect on green rice leafhopper

The respective wettable powders of the compounds (1) shown in Table 2 prepared as in Example 2 were diluted to 300 ppm with water containing a surfactant (0.01%). In these respective chemicals, young seedlings of rice were dipped for 30 seconds, respectively, air-dried and put into the respective glass cylinders.

Subsequently, 10 green rice leafhoppers (4th instar nymphs) were placed in the respective cylinders. The cylinders were closed with porous caps and left to stand in a thermostat chamber at 25° C. After 4 days, insecticidal rate was determined by counting living and dead insects.

The evaluation results of the insecticidal effect of the present compounds and the comparative compounds described in the above (1) are shown in Table 6 according to the 4 rank evaluation method.

TABLE 7

| Test of effect on green rice leafhopper | |
|---|---|
| Compound | Effect |
| 1 | A |
| 6 | A |
| 10 | A |
| 14 | A |
| 15 | A |
| 16 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 33 | A |
| 34 | A |
| 38 | A |
| 40 | A |
| 43 | A |
| 47 | A |
| 50 | A |
| 51 | A |
| 52 | A |
| 53 | A |
| 54 | A |
| 56 | A |
| 58 | A |
| 59 | A |
| 60 | A |
| 66 | A |
| 67 | A |
| 68 | A |
| 69 | A |
| 70 | A |
| 71 | A |
| 73 | A |
| 74 | A |
| 75 | A |
| 77 | A |
| 78 | A |
| 79 | A |
| 80 | A |
| 81 | A |
| 83 | A |
| 84 | A |
| 85 | A |
| 86 | A |
| 87 | A |
| 88 | A |
| 90 | A |
| 91 | A |
| 92 | A |
| 93 | A |
| 111 | A |
| Comparative compound 1 | D |
| Comparative compound 2 | D |
| Comparative compound 3 | D |
| Comparative compound 7 | D |

TABLE 7-continued

| Test of effect on green rice leafhopper | |
|---|---|
| Compound | Effect |
| Comparative compound 6 | D |

(4) Test of effect on two-spotted spider mite female adult

The respective wettable powders of the compounds (1) shown in Table 2 prepared as in Example 2 were diluted to 300 ppm with water containing a surfactant (0.01%), and in these respective chemicals, kidney bean leaves (diameter: 20 mm) on which 10 two-spotted spider mite female adults were parasitic were dipped for 15 seconds, respectively.

Subsequently, these respective leaves were left to stand in a thermostat chamber at 25° C, and after 3 days, acaricidal rate was determined by counting living and dead mites in the respective leaves.

The acaricidal effect was evaluated by using 4 ranks depending on the range of acaricidal rate (A: 100%, B: less than 100 to 80%, C: less than 80 to 60% and D: less than 60%).

The evaluation results of the acaricidal effect of the present compounds and the comparative compounds described in the above (1) are shown in Table 8.

TABLE 8

| Test of effect on two-spotted spider mite female adult | |
|---|---|
| Compound | Effect |
| 1 | A |
| 6 | A |
| 7 | B |
| 10 | A |
| 14 | A |
| 15 | A |
| 19 | B |
| 20 | B |
| 21 | A |
| 23 | A |
| 25 | A |
| 29 | B |
| 33 | A |
| 34 | A |
| 38 | A |
| 43 | A |
| 51 | A |
| 56 | A |
| 58 | B |
| 62 | A |
| 65 | B |
| 66 | A |
| 67 | B |
| 68 | B |
| 69 | A |
| 70 | B |
| 71 | A |
| 72 | A |
| 73 | A |
| 74 | B |
| 75 | A |
| 77 | A |
| 79 | A |
| 81 | A |
| 83 | A |
| 84 | A |
| 87 | A |
| 90 | B |
| 91 | B |
| 93 | A |

TABLE 8-continued

Test of effect on two-spotted spider mite female adult

| Compound | Effect |
|---|---|
| 111 | A |
| Comparative compound 1 | D |
| Comparative compound 2 | D |
| Comparative compound 3 | D |
| Comparative compound 4 | D |
| Comparative compound 6 | D |
| Comparative compound 7 | D |

(5) Test of effect on southern root-knot nematode

The respective wettable powders of the compounds (1) shown in Table 2 prepared as in Example 2 were diluted to 10 ppm with water containing a surfactant (0.01%), and in these respective chemicals, 100 southern root-knot nematodes (secondary larvae) were placed.

Subsequently, the chemicals were left to stand in a thermostat chamber at 25° C., and after 2 days, nematocidal rate was determined by counting living and dead nematodes with a microscope.

The nematocidal effect was evaluated by using 4 ranks depending on the range of nematocidal rate (A: 100% B: less than 100 to 80%, C: less than 80 to 60% and D: less than 60%).

For comparison, Comparative compounds 1 to 3 shown in Table 3 were evaluated in the same manner as in the compounds (1).

The results are shown in Table 9.

TABLE 9

Test of effect on southern root-knot nematode

| Compound | Effect |
|---|---|
| 6 | A |
| 10 | A |
| 14 | A |
| 15 | A |
| 16 | A |
| 20 | A |
| 21 | A |
| 23 | A |
| 24 | A |
| 25 | A |
| 28 | A |
| 29 | A |
| 33 | A |
| 34 | A |
| 38 | A |
| 40 | A |
| 43 | A |
| 47 | A |
| 48 | A |
| 49 | A |
| 51 | A |
| 52 | A |
| 54 | A |
| 58 | A |
| 59 | A |
| 60 | A |
| 69 | A |
| 70 | A |
| 71 | A |
| 73 | A |

TABLE 9-continued

Test of effect on southern root-knot nematode

| Compound | Effect |
|---|---|
| 74 | A |
| 75 | A |
| 77 | A |
| 78 | A |
| 79 | A |
| 81 | A |
| 83 | A |
| 84 | A |
| 85 | A |
| 86 | A |
| 87 | A |
| 88 | A |
| 90 | A |
| 91 | A |
| 93 | A |
| 111 | A |

(6) Test of controlling effect on powdery mildew (barley) (prevention effect)

In plastic flowerpots having a diameter of 6 cm, 10 barleys (variety: Kuromugi) were grown per one flowerpot, and to the young plants at 1.5 leaf stage, the chemicals obtained by diluting the wettable powders of the compounds (1) shown in Table 2 prepared as in Example 2 to 500 ppm with water containing a surfactant (0.01%) were sprayed in an amount of 20 ml per one flowerpot, respectively.

These barleys were grown in a glass greenhouse for 2 days, and then conidiospores of powdery mildew (barley) collected from infected leaves were dusted uniformly over the respective plants to be inoculated thereinto.

Subsequently, these plants were grown in a glass greenhouse for one week, and the degree of lesion of powdery mildew (barley) appeared on the respective first leaves was examined.

The fungicidal effect was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

The results are shown in Table 10.

TABLE 10

Test of controlling effect on powdery mildew (barley) (prevention effect)

| Compound | Effect |
|---|---|
| 1 | 5 |
| 6 | 4 |
| 10 | 5 |
| 14 | 5 |
| 16 | 5 |
| 19 | 5 |
| 21 | 4 |
| 25 | 5 |
| 33 | 5 |
| 34 | 5 |
| 42 | 5 |
| 45 | 4 |
| 46 | 4 |
| 47 | 5 |
| 49 | 5 |
| 50 | 5 |
| 51 | 5 |
| 52 | 4 |
| 53 | 4 |
| 55 | 5 |
| 56 | 5 |

TABLE 10-continued

Test of controlling effect on powdery mildew (barley) (prevention effect)

| Compound | Effect |
| --- | --- |
| 62 | 5 |
| 67 | 5 |
| 68 | 5 |
| 69 | 5 |
| 70 | 5 |
| 71 | 5 |
| 72 | 5 |
| 73 | 5 |
| 74 | 5 |
| 75 | 5 |
| 76 | 5 |
| 77 | 4 |
| 78 | 5 |
| 79 | 5 |
| 83 | 5 |
| 84 | 5 |
| 85 | 4 |
| 87 | 5 |
| Non-treated district | 0 |

(7) Test of controlling effect on brown rust (wheat) (prevention effect)

In plastic flowerpots having a diameter of 6 cm, 10 wheats (variety: Kobushi Komugi) were grown per one flowerpot, and to the young plants at 1.5 leaf stage, the chemicals obtained by diluting the wettable powders of the compounds (1) shown in Table 2 prepared as in Example 2 to 500 ppm with water containing a surfactant (0.01%) were sprayed in an amount of 20 ml per one flowerpot, respectively.

After spraying, the wheats were grown in a glass greenhouse for 2 days, and then a suspension of spores of brown rust (wheat) ($7 \times 10^4$ spores/ml) was sprayed uniformly to the plants to by inoculated thereinto.

After inoculation, the wheats were grown in a glass greenhouse for one week, and the degree of lesion of brown rust (wheat) appeared on the first leaves was examined.

The results are shown in Table 11 according to the 6 rank evaluation method described in the above (6).

TABLE 11

Test of controlling effect on brown rust (wheat) (prevention effect)

| Compound | Effect |
| --- | --- |
| 1 | 5 |
| 2 | 4 |
| 4 | 4 |
| 5 | 4 |
| 6 | 5 |
| 8 | 4 |
| 9 | 4 |
| 10 | 5 |
| 11 | 4 |
| 14 | 5 |
| 19 | 5 |
| 21 | 5 |
| 25 | 5 |
| 27 | 4 |
| 28 | 4 |
| 29 | 5 |
| 34 | 5 |
| 45 | 4 |
| 46 | 4 |
| 47 | 5 |
| 49 | 5 |
| 50 | 5 |
| 51 | 5 |
| 52 | 5 |
| 53 | 5 |
| 54 | 5 |
| 56 | 5 |
| 63 | 5 |
| 64 | 4 |
| 65 | 4 |
| 66 | 5 |
| 67 | 5 |
| 68 | 5 |
| 69 | 5 |
| 70 | 5 |
| 71 | 5 |
| 72 | 5 |
| 73 | 5 |
| 74 | 5 |
| 75 | 5 |
| 76 | 6 |
| 77 | 5 |
| 78 | 5 |
| 79 | 5 |
| 81 | 5 |
| 82 | 4 |
| 83 | 5 |
| 84 | 5 |
| 85 | 5 |
| 86 | 5 |
| 87 | 5 |
| 92 | 4 |
| Non-treated district | 0 |

The novel 4-phenethylaminopyrimidine derivative of the present invention has excellent insecticidal, acaricidal, fungicidal and nematocidal effects.

We claim:

1. A 4-phenethylaminopyrimidine compound represented by the formula (I):

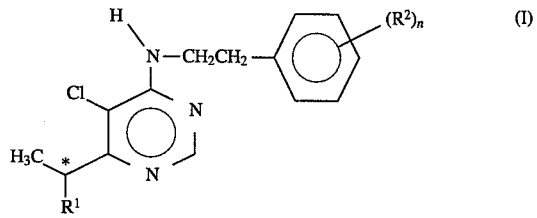

wherein $R^1$ represents a halogen atom, a hydroxyl group, an acyloxy group having 2 to 5 carbon atoms, an alkoxy group having 1 to 4 carbon atoms, a haloalkoxy group having 1 to 4 carbon atoms, an alkylthio group having 1 to 4 carbon atoms, a benzyloxycarbonyloxy group, an alkyloxycarbonyloxy group having 2 to 5 carbon atoms, an alkylsulfonyloxy group having 1 to 4 carbon atoms, a tri($C_{1-4}$ alkyl)silyloxy group or an alkyloxycarbonylalkyloxy group having 3 to 6 carbon atoms;

$R^2$ represents a hydrogen atom, an alkyl group having 1 to 4 carbon atoms, an alkoxy group having 1 to 4 carbon atoms, a halogen atom, a haloalkyl group having 1 to 4 carbon atoms, a haloalkoxy group having 1 to 4 carbon atoms, a benzoyl group which is unsubstituted or substituted by at least one of a halogen atom, an alkyl group having 1 to 4 carbon atoms, an alkoxy group having 1 to 4 carbon atoms, a haloalkyl group having 1 to 4 carbon atoms and an alkylthio group having 1 to 4 carbon atoms, a hydroxyl group, a haloalkylcarbonyl group having 2 to 5 carbon atoms, an alkylsulfonyloxy group having 1 to 4 carbon atoms, a haloalkylsulfonyloxy group having 1 to 4 carbon atoms, an alkylsulfonyl group having 1 to 4 carbon atoms, an alkylsulfinyl group having 1 to 4 carbon atoms, a haloalkylsulfinyl group having 1 to 4 carbon atoms, a tri ($C_{1-4}$ alkyl)silylalkoxy group having 1 to 4 alkoxy carbon atoms, an alkylthio group having 1 to 4 carbon atoms, a pyridyloxy group which is unsubstituted or substituted by at least one of a halogen atom and a haloalkyl group having 1 to 4 carbon atoms, a phenoxy group which is unsubstituted or substituted by at least one of a halogen atom and a haloalkyl group having 1 to 4 carbon atoms, an alkenyloxy group having 2 to 5 carbon atoms, a haloalkenyloxy group having 2 to 5 carbon atoms, a benzyl group which is unsubstituted or substituted by at least one of a halogen atom and a hydroxyl group, a 2-phenyl-2-1,3-dioxolanyl group, an alkoxyiminobenzyl group, a dialkylhydrazonobenzyl group, a nitro group, a haloalkylthio group having 1 to 4 carbon atoms, or an alkynyloxy group having 2 to 5 carbon atoms;

n is an integer of 1 to 5; and

* represents an asymmetric carbon atom.

2. The compound according to claim 1, wherein $R^1$ is selected from the group consisting of a chlorine atom, an iodine atom, a bromine atom, a fluorine atom, a hydroxyl group, an acyloxy group having 2 to 4 carbon atoms, a methoxy group, a straight or branched alkoxy group substituted by at least one of a chlorine atom, an iodine atom, a bromine atom and a fluorine atom, a methylthio group, a benzyloxycarbonyloxy group, a tert-butoxycarbonyloxy group, a methylsulfonyloxy group, a trimethylsilyloxy group and a methylcarbonyloxymethoxy group.

3. The compound according to claim 1, wherein $R^1$ is selected from the group consisting of a fluorine atom, a chlorine atom, a hydroxyl group, an acetyloxy group, a methoxy group, —$OCF_2CHFCF_3$, —$OCF_2CHFCl$, a methylthio group, a benzyloxycarbonyloxy group, a tert-butoxycarbonyloxy group, a methylsulfonyloxy group, a trimethylsilyloxy group and a methylcarbonyloxymethoxy group.

4. The compound according to claim 1, wherein $R^2$ is at least one selected from the group consisting of a hydrogen atom, a methyl group, a methoxy group, an ethoxy group, a chlorine atom, an iodine atom, a bromine atom, a fluorine atom, a trifluoromethyl group, —$OCF_3$, —$OCHF_2$, —$OCH_2CF_3$, —$OCF_2CHFCF_3$, —$OCHFCHF_2$, —$OCF_2CHFCl$, a benzoyl group which is unsubstituted or substituted by at least one of a chlorine atom, an iodine atom, a bromine atom, a fluorine atom, a methyl group, a methoxy group, a trifluoromethyl group and a methylthio group, a hydroxyl group, a trifluoromethylcarbonyl group, a methylsulfonyloxy group, a trifluoromethylsulfonyloxy group, a methylsulfonyl group, a methylsulfinyl group, a fluoromethylsulfinyloxy group, a trimethylsilylmethoxy group, a methylthio group, a pyridyloxy group which is unsubstituted or substituted by at least one of a chlorine atom, an iodine atom, a bromine atom, a fluorine atom, a methyl group and a methyl group substituted by at least one of a chlorine atom, an iodine atom, a bromine atom and a fluorine atom, a phenoxy group which is unsubstituted or substituted by at least one of a chlorine atom, an iodine atom, a bromine atom, a fluorine atom and a methyl group substituted by at least one of a chlorine atom, an iodine atom, a bromine atom and a fluorine atom, an allyoxy group, —$OCH=CH—CH=CF_2$, —$OCH_2CH_2—CF=CF_2$, a benzyl group which is unsubstituted or substituted by at least one of a chlorine atom, an iodine atom, a bromine atom, a fluorine atom or a hydroxyl group, a 2-phenyl-2-1,3-dioxolanyl group, a methoxyiminobenzyl group, a dimethylhydrazonobenzyl group, a nitro group, a 2,2,2-trifluoroethylthio group or a —$OCH_2C\equiv CH$.

5. The compound according to claim 1, wherein $R^2$ is at least one selected from the group consisting of a hydrogen atom, a methyl group, a methoxy group, an ethoxy group, a fluorine atom, a chlorine atom, a trifluoromethyl group, —$OCF_3$, —$OCHF_2$, —$OCH_2CF_3$, —$OCF_2CHFCF_3$, —$OCHFCHF_2$, —$OCF_2CHFC_1$, a benzoyl group which is unsubstituted or substituted by at least one of a chlorine atom, a fluorine atom, a methyl group, a methoxy group, a trifluoromethyl group and a methylthio group, a hydroxyl group, a trifluoromethylcarbonyl group, a methylsulfonyloxy group, a trifluoromethylsulfonyloxy group, a methylsulfonyl group, a methylsulfinyl group, a fluoromethylsulfinyloxy group, a trimethylsilylmethoxy group, a methylthio group, a pyridyloxy group which is unsubstituted or substituted by at least one of a chlorine atom and a trifluoromethyl group, a phenoxy group which is unsubstituted or substituted by at least one of a chlorine atom and a trifluoromethyl group, an allyoxy group, —$OCH=CH—CH=CF_2$, —$OCH_2CH_2—CF=CF_2$, a benzyl group which is unsubstituted or substituted by at least one of a chlorine atom, a fluorine atom and a hydroxyl group, a 2-phenyl-2-1,3-dioxolanyl group, a methoxyiminobenzyl group, a dimethylhydrazonobenzyl group, a nitro group, a 2,2,2-trifluoroethylthio group or —$OCH_2C\equiv CH$.

6. The compound according to claim 1, wherein the compound of the formula (I) is selected from the group consisting of:

(1) a compound in which $R^1$ is a halogen atom and $R^2$ is a hydrogen atom;

(2) a compound in which $R^1$ is a hydroxyl group and $R^2$ is a hydrogen atom;

(3) a compound in which $R^1$ is an acyloxy group having 2 to 5 carbon atoms and $R^2$ is an alkyl group having 1 to 4 carbon atoms;

(4) a compound in which $R^1$ is a hydroxyl group and $R^2$ is an alkyl group having 1 to 4 carbon atoms;

(5) a compound in which $R^1$ is a halogen atom and $R^2$ is an alkyl group having 1 to 4 carbon atoms;

(6) a compound in which $R^1$ is a halogen atom and $R^2$ is an alkoxy group having 1 to 4 carbon atoms;

(7) a compound in which $R^1$ is an acyloxy group having 2 to 5 carbon atoms and $R^2$ is an alkoxy group having 1 to 4 carbon atoms;

(8) a compound in which $R^1$ is a hydroxyl group and $R^2$ is an alkoxy group having 1 to 4 carbon atoms;

(9) a compound in which $R^1$ and $R^2$ are halogen atoms;
(10) a compound in which $R^1$ is a halogen atom and $R^2$ is a benzoyl group;
(11) a compound in which $R^1$ is an acyloxy group having 2 to 5 carbon atoms and $R^2$ is a benzoyl group;
(12) a compound in which $R^1$ is a hydroxyl group and $R^2$ is a benzoyl group;
(13) a compound in which $R^1$ is a halogen atom and $R^2$ is a haloalkyl group having 1 to 4 carbon atoms;
(14) a compound in which $R^1$ is a halogen atom and $R^2$ is a haloalkoxy group having 1 to 4 carbon atoms;
(15) a compound in which $R^1$ is an alkylthio group having 1 to 4 carbon atoms and $R^2$ is a benzoyl group;
(16) a compound in which $R^1$ is a halogen atom and $R^2$ is a haloalkylcarbonyl group having 2 to 5 carbon atoms;
(17) a compound in which $R^1$ is an acyloxy group having 2 to 5 carbon atoms and $R^2$ is an alkylsulfonyloxy group having 1 to 4 carbon atoms;
(18) a compound in which $R^1$ is a hydroxyl group and $R^2$ is an alkylsulfonyloxy group having 1 to 4 carbon atoms;
(19) a compound in which $R^1$ is a halogen atom and $R^2$ is an alkylsulfonyloxy group having 1 to 4 carbon atoms;
(20) a compound in which $R^1$ is an acyloxy group having 2 to 5 carbon atoms and $R^2$ is a haloalkoxy group having 1 to 4 carbon atoms;
(21) a compound in which $R^1$ is a hydroxyl group and $R^2$ is a haloalkoxy group having 1 to 4 carbon atoms;
(22) a compound in which $R^1$ is an alkoxy group having 1 to 4 carbon atoms and $R^2$ is a haloalkoxy group having 1 to 4 carbon atoms;
(23) a compound in which $R^1$ is a benzyloxycarbonyloxy group and $R^2$ is a haloalkoxy group having 1 to 4 carbon atoms;
(24) a compound in which $R^1$ is an alkyloxycarbonyloxy group having 2 to 5 carbon atoms and $R^2$ is a haloalkoxy group having 1 to 4 carbon atoms;
(25) a compound in which $R^1$ is a halogen atom and $R^2$ is a haloalkylsulfonyloxy group having 1 to 4 carbon atoms;
(26) a compound in which $R^1$ is an acyloxy group having 2 to 5 carbon atoms and $R^2$ is a haloalkylsulfonyloxy group having 1 to 4 carbon atoms;
(27) a compound in which $R^1$ is an alkylsulfonyloxy group having 1 to 4 carbon atoms and $R^2$ is a benzoyl group;
(28) a compound in which $R^1$ is a tri($C_{1-4}$ alkyl)silyloxy group and $R^2$ is a benzoyl group;
(29) a compound in which $R^1$ is an acyloxy group having 2 to 5 carbon atoms and $R^2$ is a haloalkyl group having 1 to 4 carbon atoms;
(30) a compound in which $R^1$ is a hydroxyl group and $R^2$ is a haloalkyl group having 1 to 4 carbon atoms;
(31) a compound in which $R^1$ is a halogen atom and $R^2$ is an alkoxyiminobenzyl group;
(32) a compound in which $R^1$ is a halogen atom and $R^2$ is a 2-phenyl-2-1,3-dioxolanyl group;
(33) a compound in which $R^1$ is a halogen atom and $R^2$ is a benzyl group;
(34) a compound in which $R^1$ is a haloalkoxy group having 1 to 4 carbon atoms and $R^2$ is a haloalkoxy group having 1 to 4 carbon atoms;
(35) a compound in which $R^1$ is a halogen atom and $R^2$ is a phenoxy group;
(36) a compound in which $R^1$ is a halogen atom and $R^2$ is a haloalkenyloxy group having 2 to 5 carbon atoms;
(37) a compound in which $R^1$ is a halogen atom and $R^2$ is an alkenyloxy group having 2 to 5 carbon atoms;
(38) a compound in which $R^1$ is a halogen atom and $R^2$ is a tri($C_{1-4}$ alkyl)silylalkoxy group having 1 to 4 alkoxy carbon atoms;
(39) a compound in which $R^1$ is a halogen atom and $R^2$ is an alkylthio group having 1 to 4 carbon atoms;
(40) a compound in which $R^1$ is a halogen atom and $R^2$ is a hydroxyl group;
(41) a compound in which $R^1$ is a halogen atom and $R^2$ is an alkylsulfonyl group having 1 to 4 carbon atoms;
(42) a compound in which $R^1$ is a halogen atom and $R^2$ is an alkylsulfinyl group having 1 to 4 carbon atoms;
(43) a compound in which $R^1$ is a halogen atom and $R^2$ is a pyridyloxy group;
(44) a compound in which $R^1$ is a halogen atom and $R^2$ is a haloalkylsulfinyl group having 1 to 4 carbon atoms;
(45) a compound in which $R^1$ is a halogen atom and $R^2$ is a dialkylhydrazonobenzyl group;
(46) a compound in which $R^1$ is a hydroxyl group and $R^2$ is an α-hydroxybenzyl group; and
(47) a compound in which $R^1$ is a halogen atom and $R^2$ is a nitro group.

7. The compound according to claim 1, wherein said compound is selected from the group consisting of a compound in which:

$R^1$ is a hydroxyl group and $R^2$ is $-CO-C_6H_4Cl$;

$R^1$ is a fluorine atom and the $R_2$s are $-CH_3$ and $-OCH_2CH_3$;

$R^1$ is a fluorine atom and $R^2$ is
a hydrogen atom, $-CH_3$, $-OCH_3$,
a fluorine atom, a chlorine atom, $-COC_6H_5$, $-CO-C_6H_4Cl$, $-COC_6H_4CH_3$, $-CF_3$, $-OCHF_2$, $-COCF_3$, $-OSO_2CH_3$, $-OCH_2CF_3$, $-OSO_2CF_3$,

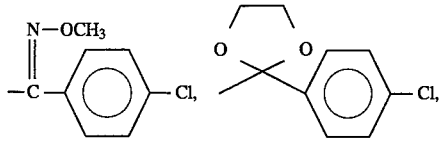

$-CHFC_6H_4Cl$, $-OCF_2CHFCF_3$, $-OCHFCHF_2$, $-OC_6F_5$, $-OCF_2CHFCl$, $-OCH=CH-CH=CF_2$, $-OC_2H_5$, $-OCH_2CH=CH_2$, $-OSH_2Si(CH_3)_3$, $-SCH_3$, $-OH$, $-OC_6H_4CF_3$, $-t-C_4H_9$, $-SO_2CH_3$, $-SOCH_3$,

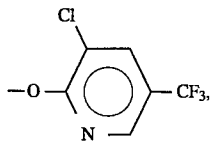

$-SOCH_2F$, $-OCF_3$, or $-NO_2$.

8. An agricultural and horticultural composition for controlling noxious organisms comprising the compound represented by the formula (I) according to claim 1 as an active ingredient and an insecticidally, acaricidally, fungicidally or nematocidally compatible inert carrier.

* * * * *